(12) United States Patent
Blott et al.

(10) Patent No.: US 11,147,714 B2
(45) Date of Patent: Oct. 19, 2021

(54) WOUND TREATMENT APPARATUS AND METHOD

(71) Applicant: Smith & Nephew PLC, Watford (GB)

(72) Inventors: Patrick Lewis Blott, York (GB); Clare Green, York (GB); Edward Yerbury Hartwell, Hull (GB); Robin Paul Martin, Selby (GB); Derek Nicolini, Brough (GB); Julian Lee-Webb, York (GB)

(73) Assignee: Smith & Nephew PLC, Watford (GB)

( * ) Notice: Subject to any disclaimer, the term of this patent is extended or adjusted under 35 U.S.C. 154(b) by 189 days.

(21) Appl. No.: 16/045,622

(22) Filed: Jul. 25, 2018

(65) Prior Publication Data

US 2019/0015648 A1 Jan. 17, 2019

Related U.S. Application Data

(63) Continuation of application No. 14/715,220, filed on May 18, 2015, now Pat. No. 10,035,006, which is a (Continued)

(30) Foreign Application Priority Data

Apr. 27, 2005 (GB) ...................................... 0508531

(51) Int. Cl.
*A61F 13/00* (2006.01)
*A61F 13/02* (2006.01)
(Continued)

(52) U.S. Cl.
CPC .... *A61F 13/0216* (2013.01); *A61F 13/00068* (2013.01); *A61F 13/02* (2013.01);
(Continued)

(58) Field of Classification Search
CPC ................ A61F 13/00068; A61F 13/02; A61F 2013/00536; A61M 1/0058;
(Continued)

(56) References Cited

U.S. PATENT DOCUMENTS

| | | | |
|---|---|---|---|
| 1,355,846 A | * | 10/1920 | Rannells ............. A61F 13/2048 604/286 |
| 2,280,915 A | | 4/1942 | Johnson |
| 3,367,332 A | | 2/1968 | Groves |
| 3,624,821 A | | 11/1971 | Henderson |
| 3,874,387 A | | 4/1975 | Barbieri |

(Continued)

FOREIGN PATENT DOCUMENTS

| | | |
|---|---|---|
| DE | 3 935 818 | 5/1991 |
| DE | 4 012 232 | 10/1991 |
| DE | 4 102 684 | 8/1992 |
| DE | 198 44 355 | 4/2000 |

(Continued)

OTHER PUBLICATIONS

Aubrey, D.A., et al., "Treatment of the Perineal Wound after Proctectomy by Intermittent Irrigation", Arch. Surg., vol. 119, Oct. 1984, pp. 1141-1144, in 4 pages.

(Continued)

*Primary Examiner* — William R Carpenter
(74) *Attorney, Agent, or Firm* — Knobbe, Martens, Olson & Bear, LLP

(57) ABSTRACT

An apparatus for cleansing wounds in which irrigant fluid from a reservoir connected to a conformable wound dressing and wound exudate from the dressing are moved by a device (which may be a single pump or two pumps) for moving fluid through a flow path which passes through the dressing and a means for providing simultaneous aspiration and irrigation of the wound. The apparatus also comprises means to apply high frequency vibrational energy, e.g. ultrasound, to the wound bed. The former removes materials deleterious to wound healing, while distributing materials that are (Continued)

beneficial in promoting wound healing over the wound bed. The latter promotes healing. The dressing and a method of treatment using the apparatus.

10 Claims, 13 Drawing Sheets

Related U.S. Application Data continuation of application No. 11/919,354, filed as application No. PCT/GB2006/001552 on Apr. 27, 2006, now Pat. No. 9,044,579.

(51) Int. Cl.
| | | |
|---|---|---|
| A61M 1/00 | (2006.01) | |
| A61M 3/02 | (2006.01) | |
| A61N 7/00 | (2006.01) | |
| A61M 35/00 | (2006.01) | |

(52) U.S. Cl.
CPC ....... *A61F 13/0226* (2013.01); *A61M 1/0058* (2013.01); *A61M 1/85* (2021.05); *A61M 1/90* (2021.05); *A61M 3/02* (2013.01); *A61M 3/022* (2014.02); *A61M 3/0208* (2014.02); *A61M 3/0212* (2014.02); *A61M 35/30* (2019.05); *A61N 7/00* (2013.01); *A61F 2013/00536* (2013.01); *A61M 2205/058* (2013.01); *A61N 2007/0017* (2013.01)

(58) Field of Classification Search
CPC .............. A61M 1/0084; A61M 1/0088; A61M 2205/058; A61N 2007/0017
See application file for complete search history.

(56) References Cited

U.S. PATENT DOCUMENTS

| | | |
|---|---|---|
| 3,993,080 A | 11/1976 | Loseff |
| 4,112,947 A | 9/1978 | Nehring |
| 4,136,696 A | 1/1979 | Nehring |
| 4,178,938 A | 12/1979 | Au |
| 4,180,074 A | 12/1979 | Murry et al. |
| 4,184,510 A | 1/1980 | Murry et al. |
| 4,224,945 A | 9/1980 | Cohen |
| 4,316,466 A | 2/1982 | Babb |
| 4,382,441 A | 5/1983 | Svedman |
| 4,465,485 A | 8/1984 | Kashmer et al. |
| 4,466,431 A | 8/1984 | Tharrat et al. |
| 4,508,256 A | 4/1985 | Radek et al. |
| 4,530,360 A | 7/1985 | Duarte |
| 4,573,965 A | 3/1986 | Russo |
| 4,778,446 A | 10/1988 | Jensen |
| 4,787,888 A | 11/1988 | Fox |
| 4,792,328 A | 12/1988 | Beck et al. |
| 4,921,488 A | 5/1990 | Maitz et al. |
| 4,936,834 A | 6/1990 | Beck et al. |
| 4,969,880 A | 11/1990 | Zamierowski |
| 5,055,198 A | 10/1991 | Shettigar |
| 5,073,172 A | 12/1991 | Fell |
| 5,078,144 A | 1/1992 | Sekino et al. |
| 5,100,396 A | 3/1992 | Zamierowski |
| 5,112,323 A | 5/1992 | Winkler et al. |
| 5,176,663 A | 1/1993 | Svedman et al. |
| 5,261,893 A | 11/1993 | Zamierowski |
| 5,328,614 A | 7/1994 | Matsumura |
| 5,358,494 A | 10/1994 | Svedman |
| 5,360,398 A | 11/1994 | Grieshaber et al. |
| 5,380,280 A | 1/1995 | Peterson |
| 5,498,338 A | 3/1996 | Kruger et al. |
| 5,549,584 A | 8/1996 | Gross |
| 5,636,643 A | 6/1997 | Argenta et al. |
| 5,645,081 A | 7/1997 | Argenta et al. |
| 5,676,650 A | 10/1997 | Grieshaber et al. |
| 5,759,570 A | 6/1998 | Arnold |
| 5,810,765 A | 9/1998 | Oda |
| 5,830,176 A | 11/1998 | Mackool |
| 5,904,659 A | 5/1999 | Duarte |
| 5,964,723 A | 10/1999 | Augustine |
| 6,071,267 A | 6/2000 | Zamierowski |
| 6,254,567 B1 | 7/2001 | Treu et al. |
| 6,398,767 B1 | 6/2002 | Fleischmann |
| 6,458,109 B1 | 10/2002 | Henley et al. |
| 6,465,708 B1 | 10/2002 | Augustine |
| 6,626,827 B1 | 9/2003 | Felix et al. |
| 6,676,610 B2 | 1/2004 | Morton et al. |
| 6,685,681 B2 | 2/2004 | Lockwood et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 7,077,832 B2 | 7/2006 | Fleischmann |
| 7,108,683 B2 | 9/2006 | Zamierowski |
| 7,195,624 B2 | 3/2007 | Lockwood |
| 7,211,060 B1 | 5/2007 | Talish et al. |
| 7,216,651 B2 | 5/2007 | Argenta et al. |
| D543,691 S | 6/2007 | Payne et al. |
| D548,347 S | 8/2007 | Ichino et al. |
| 7,381,859 B2 | 6/2008 | Hunt et al. |
| 7,381,860 B2 | 6/2008 | Gundnason et al. |
| 7,494,482 B2 | 2/2009 | Orgill et al. |
| 7,524,315 B2 | 4/2009 | Blott et al. |
| 7,532,953 B2 | 5/2009 | Vogel |
| 7,534,927 B2 | 5/2009 | Lockwood |
| 7,569,742 B2 | 8/2009 | Haggstrom et al. |
| 7,604,610 B2 | 10/2009 | Shener et al. |
| 7,628,764 B2 | 12/2009 | Duarte et al. |
| 7,648,488 B2 | 1/2010 | Smith et al. |
| 7,670,323 B2 | 3/2010 | Hunt et al. |
| 7,686,785 B2 | 3/2010 | Boehringer et al. |
| 7,699,830 B2 | 4/2010 | Martin |
| 7,731,702 B2 | 6/2010 | Bybordi et al. |
| 7,753,894 B2 | 7/2010 | Blott et al. |
| 7,759,538 B2 | 7/2010 | Fleischmann |
| 7,767,936 B2 | 8/2010 | Ferguson |
| 7,794,438 B2 | 9/2010 | Henley et al. |
| 7,794,450 B2 | 9/2010 | Blott et al. |
| 7,812,212 B2 | 10/2010 | Propp et al. |
| 7,828,782 B2 | 11/2010 | Suzuki |
| 7,838,717 B2 | 11/2010 | Haggstrom et al. |
| 7,883,494 B2 | 2/2011 | Martin |
| 7,909,805 B2 | 3/2011 | Weston |
| 7,954,672 B2 | 6/2011 | Keller |
| 7,964,766 B2 | 6/2011 | Blott et al. |
| 7,981,098 B2 | 7/2011 | Boehringer et al. |
| 8,074,843 B2 | 12/2011 | Keller |
| 8,075,503 B2 * | 12/2011 | Jaeb .................. A61M 1/0088 601/2 |
| 8,080,702 B2 | 12/2011 | Blott et al. |
| 8,105,295 B2 | 1/2012 | Blott et al. |
| 8,114,126 B2 | 2/2012 | Heaton et al. |
| 8,128,615 B2 | 3/2012 | Blott et al. |
| 8,162,909 B2 | 4/2012 | Blott et al. |
| 8,187,237 B2 | 5/2012 | Seegert |
| 8,207,392 B2 | 6/2012 | Haggstrom et al. |
| 8,235,955 B2 | 8/2012 | Blott et al. |
| 8,257,327 B2 | 9/2012 | Blott et al. |
| 8,286,832 B2 | 10/2012 | Keller |
| 8,338,402 B2 | 12/2012 | Fry et al. |
| 8,348,910 B2 | 1/2013 | Blott et al. |
| 8,372,049 B2 | 2/2013 | Jaeb et al. |
| 8,398,614 B2 | 3/2013 | Blott et al. |
| 8,529,548 B2 | 9/2013 | Blott et al. |
| 8,529,578 B2 | 9/2013 | Daniels et al. |
| 8,535,296 B2 | 9/2013 | Blott et al. |
| 8,758,313 B2 | 6/2014 | Blott et al. |
| 8,791,316 B2 | 7/2014 | Greener |
| 8,829,263 B2 | 9/2014 | Haggstrom et al. |
| 8,843,327 B2 | 9/2014 | Vernon-Harcourt et al. |
| 8,926,592 B2 | 1/2015 | Blott et al. |
| 9,044,579 B2 | 6/2015 | Blott et al. |

(56) References Cited

U.S. PATENT DOCUMENTS

| | | |
|---|---|---|
| 10,035,006 B2 | 7/2018 | Blott et al. |
| 10,201,644 B2 | 2/2019 | Haggstrom et al. |
| 2001/0029956 A1 | 10/2001 | Argenta |
| 2001/0034499 A1 | 10/2001 | Sessions et al. |
| 2002/0016570 A1 | 2/2002 | Cartledge |
| 2002/0138036 A1 | 9/2002 | Babaev |
| 2002/0161346 A1 | 10/2002 | Lockwood et al. |
| 2003/0021775 A1 | 1/2003 | Freeman |
| 2003/0144619 A1 | 7/2003 | Augustine |
| 2003/0171675 A1* | 9/2003 | Rosenberg .......... A61M 1/0088 600/437 |
| 2004/0030304 A1* | 2/2004 | Hunt ...................... A61L 15/22 604/317 |
| 2004/0054338 A1 | 3/2004 | Bybordi et al. |
| 2005/0177190 A1 | 8/2005 | Zamierowski |
| 2006/0020234 A1 | 1/2006 | Chou et al. |
| 2007/0038172 A1 | 2/2007 | Zamierowski |
| 2007/0185463 A1 | 8/2007 | Mulligan |
| 2007/0219471 A1 | 9/2007 | Johnson et al. |
| 2007/0239078 A1 | 10/2007 | Jaeb |
| 2007/0248958 A1 | 10/2007 | Jovanovich et al. |
| 2007/0260226 A1 | 11/2007 | Jaeb et al. |
| 2008/0226720 A1 | 9/2008 | Kemp et al. |
| 2008/0312572 A1 | 12/2008 | Riesinger |
| 2009/0054855 A1 | 2/2009 | Blott et al. |
| 2009/0105671 A1 | 4/2009 | Daggar et al. |
| 2009/0157016 A1 | 6/2009 | Adahan |
| 2009/0157017 A1 | 6/2009 | Ambrosio |
| 2009/0163882 A1 | 6/2009 | Koch et al. |
| 2009/0221977 A1 | 9/2009 | Blott et al. |
| 2009/0299255 A1 | 12/2009 | Kazala, Jr. et al. |
| 2009/0312723 A1 | 12/2009 | Blott et al. |
| 2010/0063484 A1 | 3/2010 | Heagle |
| 2010/0069850 A1 | 3/2010 | Fabo |
| 2010/0094234 A1 | 4/2010 | Ramella et al. |
| 2010/0122417 A1 | 5/2010 | Vrzalik et al. |
| 2010/0249733 A9 | 9/2010 | Blott et al. |
| 2011/0004171 A1 | 1/2011 | Blott et al. |
| 2011/0054423 A1 | 3/2011 | Blott et al. |
| 2012/0302976 A1 | 11/2012 | Locke et al. |
| 2013/0310781 A1 | 11/2013 | Phillips et al. |
| 2015/0159066 A1 | 6/2015 | Hartwell et al. |
| 2017/0274195 A1 | 9/2017 | Blott et al. |

FOREIGN PATENT DOCUMENTS

| | | |
|---|---|---|
| EP | 0 020 662 | 7/1984 |
| EP | 0 355 186 | 2/1990 |
| EP | 0 853 950 | 7/1998 |
| EP | 0 777 504 | 10/1998 |
| EP | 0 774 242 | 3/2000 |
| EP | 0 674 892 | 7/2001 |
| EP | 0 948 951 | 6/2002 |
| EP | 0 729 334 | 3/2003 |
| EP | 0 880 953 | 10/2003 |
| EP | 1 488 816 | 12/2004 |
| EP | 0 898 471 | 5/2005 |
| EP | 1 314 410 | 2/2010 |
| EP | 2 366 721 | 9/2011 |
| FR | 1 163 907 | 10/1958 |
| GB | 114754 | 4/1918 |
| GB | 641061 | 8/1950 |
| GB | 1224009 | 3/1971 |
| GB | 1549756 | 8/1979 |
| GB | 2195255 | 4/1988 |
| GB | 2378392 | 2/2003 |
| JP | 2001-314479 | 11/2001 |
| SU | 1251912 A1 | 8/1986 |
| WO | WO 1984/01904 | 5/1984 |
| WO | WO 1990/11795 | 10/1990 |
| WO | WO 1991/000718 | 1/1991 |
| WO | WO 1992/19313 | 11/1992 |
| WO | WO 1992/020299 | 11/1992 |
| WO | WO 1999/048621 | 9/1999 |
| WO | WO 1999/056829 | 11/1999 |
| WO | WO 2000/007653 | 2/2000 |
| WO | WO 2000/50143 | 8/2000 |
| WO | WO 2001/037773 | 5/2001 |
| WO | WO 2002/083046 | 10/2002 |
| WO | WO 2002/092783 | 11/2002 |
| WO | WO 2003/074100 | 9/2003 |
| WO | WO 2004/024300 | 3/2004 |
| WO | WO 2004/037334 | 5/2004 |
| WO | WO 2005/016179 | 2/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/105174 | 11/2005 |
| WO | WO 2005/105175 | 11/2005 |
| WO | WO 2005/105176 | 11/2005 |
| WO | WO 2005/105180 | 11/2005 |
| WO | WO 2006/052338 | 5/2006 |
| WO | WO 2006/099137 | 9/2006 |
| WO | WO 2006/131747 | 12/2006 |
| WO | WO 2006/135506 | 12/2006 |
| WO | WO 2007/003905 | 1/2007 |
| WO | WO 2007/006306 | 1/2007 |
| WO | WO 2007/013049 | 2/2007 |
| WO | WO 2007/013064 | 2/2007 |
| WO | WO 2007/016590 | 2/2007 |
| WO | WO 2007/030599 | 3/2007 |
| WO | WO 2007/030601 | 3/2007 |
| WO | WO 2007/070570 | 6/2007 |
| WO | WO 2007/084792 | 7/2007 |
| WO | WO 2007/085396 | 8/2007 |
| WO | WO 2007/088530 | 8/2007 |
| WO | WO 2007/089103 | 8/2007 |
| WO | WO 2007/092397 | 8/2007 |
| WO | WO 2007/095180 | 8/2007 |
| WO | WO 2007/103208 | 9/2007 |
| WO | WO 2007/106591 | 9/2007 |
| WO | WO 2007/106594 | 9/2007 |
| WO | WO 2007/123451 | 11/2007 |
| WO | WO 2007/124198 | 11/2007 |
| WO | WO 2008/008032 | 1/2008 |
| WO | WO 2008/010094 | 1/2008 |
| WO | WO 2008/027449 | 3/2008 |
| WO | WO 2008/100437 | 8/2008 |
| WO | WO 2008/100446 | 8/2008 |
| WO | WO 2008/131895 | 11/2008 |
| WO | WO 2009/002260 | 12/2008 |
| WO | WO 2009/111655 | 9/2009 |
| WO | WO 2009/126103 | 10/2009 |
| WO | WO 2009/140376 | 11/2009 |
| WO | WO 2009/141820 | 11/2009 |
| WO | WO 2009/146441 | 12/2009 |
| WO | WO 2009/158127 | 12/2009 |
| WO | WO 2010/006182 | 1/2010 |
| WO | WO 2010/014177 | 2/2010 |
| WO | WO 2010/033769 | 3/2010 |
| WO | WO 2010/042240 | 4/2010 |
| WO | WO 2010/051073 | 5/2010 |
| WO | WO 2010/059712 | 5/2010 |
| WO | WO 2010/059730 | 5/2010 |
| WO | WO 2010/078166 | 7/2010 |
| WO | WO 2011/049562 | 4/2011 |
| WO | WO 2011/100851 | 8/2011 |
| WO | WO 2011/115908 | 9/2011 |
| WO | WO 2012/142002 | 10/2012 |
| WO | WO 2012/174672 | 12/2012 |
| WO | WO 2013/013938 | 1/2013 |
| WO | WO 2013/016239 | 1/2013 |
| WO | WO 2013/019438 | 2/2013 |
| WO | WO 2014/184674 | 11/2014 |

OTHER PUBLICATIONS

Australian Office Action, re AU Application No. 2006238957, which is the Australian National Phase Application for PCT Application No. PCT/GB2006/001552, dated Nov. 23, 2010 in 2 pages.

(56) References Cited

OTHER PUBLICATIONS

Bagautdinov, N.A., "Variant of External Vacuum Aspiration in the Treatment of Purulent Diseases of Soft Tissues", in Current Problems in Modern Clinical Surgery: Interdepartmental Collection, edited by V. Ye. Volkov et al. (Chuvash State University, Cheboksary, USSR 1986) pp. 94-96.

Chariker, M.E. et al., "Effective Management of Incisional and Cutaneous Fistulae with Closed Suction Wound Drainage", Contemporary Surgery, vol. 34, Jun. 1989, pp. 59-63, in 5 pages.

Chernavskii, V. A., et al., excerpt from "Free Skin Plasty of Wounds and Ulcers using the Vacuum Method", Meditsina Publishers of the Uzbek SSR, Tashkent 1970, pp. 5-37, in 33 pages.

Chinese Office Action, re CN Application No. 200680022913.7, dated Aug. 25, 2011, in 13 pages.

Chinese Patent Office; English Translation of First Office Action; Patent Application No. 200680022913.7 (dated Aug. 21, 2009).

English Translation of Chinese Office Action, re CN Application No. 200680022913.7, dated Mar. 1, 2010.

Chinese Patent Office; English Translation of Third Office Action; Patent Application No. 200680022913.7 (dated Jul. 9, 2010).

Chinese Office Action, re CN Application No. 201410245764.7, dated Aug. 7, 2017.

Dilmaghani, A. et al., "A Method for Closed Irrigation and Suction Therapy in Deep Wound Infections," Journal of Bone and Joint Surgery, 1969, vol. 51-A, No. 2, pp. 323-342, in 20 pages.

Hartz, R.S. et al., "Healing of the Perineal Wound", Arch. Surg., Apr. 1980, vol. 115, pp. 471-474, in 4 pages.

International Search Report, re PCT Application No. PCT/GB2003/04647, dated Feb. 25, 2004, in 3 pages.

International Preliminary Report on Patentability, re PCT Application No. PCT/GB2006/001552, dated Oct. 30, 2007.

International Search Report, re PCT Application No. PCT/GB2006/001552, dated Jan. 17, 2007.

Larichev, A.B., "Vacuum Therapy of Wounds and Wound Infection" (First Ed.), BlueSky Publishing, 2005, in 237 pages.

Nursing75, "Wound Suction: Better Drainage with Fewer Problems", Nursing, vol. 5, No. 10, Oct. 1975, pp. 52-55, in 4 pages.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Svedman, P., "Irrigation Treatment in Split-Thickness Skin Grafting of Intractable Leg Ulcers," Scand J. Plast. Reconstr. Surg., 19:211-213, 1985.

Svedman, P., "Irrigation Treatment of Leg Ulcers", The Lancet, Sep. 1983, pp. 532-534, in 3 pages.

Svedman, P., "A Dressing Allowing Continuous Treatment of a Biosurface", IRCS Med. Science: Biomed. Tech.; Clinic. Med.; Surg. and Transplantation, 1979, vol. 7, p. 221, in 1 page.

Svedman, P. et al., "A Dressing System Providing Fluid Supply and Suction Drainage Used for Continuous or Intermittent Irrigation", Annals of Plastic Surgery, vol. 17, No. 2, Aug. 1986, pp. 125-133, in 9 pages.

Swift, S. et al, "Quorum Sensing in Aeromonas hydrophila and Aeromonas salmonicida: Identification of LuxRI Homologs AhyRI and AsaRI and Their Cognate N-Acylhomoserine Lactone Signal Molecules," J. Bacteriol., 1997, vol. 179(17), pp. 5271-5281, in 12 pages.

Teder, H. et al., "Continuous Wound Irrigation in the Pig," Journal of Investigative Surgery, vol. 3, 1990, pp. 399-407, in 9 pages.

Tribble, D. E., "An Improved Sump Drain-Irrigation Device of Simple Construction", Archives of Surgery New York, vol. 105, Sep. 1972, in 4 pages.

Vijanto, J. and J. Raekallio, Local Hyperalimentation of Open Wounds, Br. J. surg., 1976, 63, 427-430.

Westaby, S. et al., "A Wound Irrigation Device", The Lancet, Sep. 2, 1978, pp. 503-504, in 2 pages.

Wooding-Scott, M. et al., "No Wound is Too Big for Resourceful Nurses," RN, Dec. 1988, pp. 22-25, USA, in 4 pages.

Ennis W.J. et al., "Ultrasound Therapy for Recalcitrant Diabetic Foot Ulcers: Results of a Randomized, Double-Blind, Controlled, Multicenter Study—Part 1," Index: Ostomy Wound Manage., vol. 51, Issue 8, Aug. 2005, pp. 24-39.

Eriksson S.V., et al., "A Placebo Controlled Trial of Ultrasound Therapy in Chronic Leg Ulceration," Scand. J. Rehab. Med., vol. 23, 1991, pp. 211-213.

Lundeberg T. et al., "Pulsed Ultrasound does not Improve Healing of Venous Ulcers," Scand. J. Rehab. Med., vol. 22, 1990, pp. 195-197.

Peschen M. et al., "Low-frequency Ultrasound Treatment of Chronic Venous Leg Ulcers in an Outpatient Therapy," Acta. Derm. Venereol (Stockh), 1997, vol. 77, pp. 311-314.

Riet G.T., et al., "Randomised clinical trial of ultrasound treatment for pressure ulcers," Department of Epidemiology, vol. 310, Apr. 22, 1995, pp. 1040-1041.

Weichenthal M. et al., "Low-frequency ultrasound treatment of chronic venous ulcers," Wound Repair and Regeneration, vol. 5, No. 1, Jan.-Mar. 1997, pp. 18-22.

\* cited by examiner

Section View on X-X

WOUND TREATMENT APPARATUS AND METHOD

CROSS REFERENCE TO RELATED APPLICATIONS

This application is a continuation of U.S. patent application Ser. No. 14/715,220, filed May 18, 2015, entitled "WOUND TREATMENT APPARATUS AND METHOD," and issued as U.S. Pat. No. 10,035,006, which is a continuation of U.S. patent application Ser. No. 11/919,354, filed Nov. 19, 2008, entitled "WOUND TREATING APPARATUS AND METHOD," and issued as U.S. Pat. No. 9,044,579, which is a U.S. National Phase of PCT International Application No. PCT/GB/2006/001552, filed Apr. 27, 2006, designating the United States and published in English on Nov. 2, 2006, as International Publication No. WO 2006/114638 A2, which application claims priority to Great Britain Patent Application No. 0508531.1, filed Apr. 27, 2005. The disclosures of the prior applications are incorporated by reference herein in their entireties and should be considered a part of this application.

BACKGROUND

Technical Field

The present invention relates to apparatus and a medical wound dressing for aspirating, irrigating and/or cleansing wounds, and a method of treating wounds using such apparatus for aspirating, irrigating and/or cleansing wounds.

It relates in particular to such an apparatus, wound dressing and method that can be easily applied to a wide variety of, but in particular chronic, wounds, to cleanse them of materials that are deleterious to wound healing, whilst distributing materials that are beneficial in some therapeutic aspect, in particular to wound healing.

Description of the Related Art

Aspirating and/or irrigating apparatus are known, and tend to be used to remove wound exudate during wound therapy. In known forms of such wound therapy, aspiration and irrigation of the wound generally take place sequentially.

Each part of the therapy cycle is beneficial in promoting wound healing:

Aspiration applies a negative pressure to the wound, which is beneficial in itself in promoting wound healing by removing materials deleterious to wound healing with the wound exudate, reducing bacterial load, combating peri-wound oedema, increasing local blood flow to the wound and encouraging the formation of wound bed granulation tissue.

Irrigation cleanses wounds of materials that are deleterious to wound healing by diluting and moving wound exudate (which is typically relatively little fluid and may be of relatively high viscosity and particulate-filled.

Additionally, relatively little of beneficial materials involved in promoting wound healing (such as cytokines, enzymes, growth factors, cell matrix components, biological signalling molecules and other physiologically active components of the exudate) are present in a wound, and are not well distributed in the wound, i.e. they are not necessarily present in parts of the wound bed where they can be potentially of most benefit. These may be distributed by irrigation of the wound and thus aid in promoting wound healing.

The irrigant may additionally contain materials that are potentially or actually beneficial in respect of wound healing, such as nutrients for wound cells to aid proliferation, and gases, such as oxygen. These may be distributed by irrigation of the wound and thus aid in promoting wound healing.

If aspiration and irrigation therapy is applied sequentially to a wound, the two therapies, each of which is beneficial in promoting wound healing, can only be applied intermittently.

Thus, the wound will lose the abovementioned known beneficial effects of aspiration therapy on wound healing, at least in part, while that aspiration is suspended during irrigation.

Additionally, for a given aspirate flow, whilst materials that are potentially or actually deleterious in respect of wound healing are removed from wound exudate, the removal in a given time period of application of the total irrigate and/or aspirate therapy will normally be less effective and/or slower than with continuous application of aspiration.

Even less to be desired, is that while aspiration is not applied to the wound, wound exudate and materials deleterious to wound healing (such as bacteria and debris, and iron II and iron Ill and for chronic wounds proteases, such as serine proteases) will pool on the wound bed and hinder wound healing, especially in a highly exuding wound. The influx of local oedema will also add to the chronicity of the wound. This is especially the case in chronic wounds.

Depending on the relative volumes of irrigant and wound exudate, the mixed exudate-irrigant fluid and may be of relatively high viscosity and/or particulate-filled. Once it is present and has pooled, it may be more difficult to shift by the application of aspiration in a conventional sequential aspirate irrigate-dwell cycle than with continuous simultaneous aspiration and irrigation of the wound, owing to the viscosity and blockage in the system.

The wound will also lose the abovementioned beneficial effects of irrigation therapy on wound healing, at least in part, while that irrigation is suspended during aspiration.

These benefits in promoting wound healing include the movement of materials that are beneficial in promoting wound healing, such as those mentioned above.

Additionally, for a given irrigant flow, the Cleansing of the wound and the distribution by irrigation of the wound of such beneficial materials in a given time period of application of the total irrigate and/or aspirate therapy when such therapy is in a conventional sequential aspirate-irrigate-dwell cycle will normally be less effective and/or slower than with continuous application of aspiration.

Such known forms of aspiration and/or irrigation therapy systems also often create a wound environment that may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

SUMMARY

The relevant devices tend not to be portable.

It thus would be desirable to provide a system of aspiration and irrigation therapy for a wound, which can remove wound exudate and materials deleterious to wound healing from contact with the wound bed, whilst simultaneously cleansing it and distributing materials that are beneficial in promoting wound healing across it.

It is further desirable to provide a system which: obviates at least some of the abovementioned disadvantages of known aspiration and/or irrigation systems, and is portable.

Vascular supply to, and aspiration in, tissue underlying and surrounding the wound is often compromised.

It is further desirable to provide a system of therapy that also promotes vascular supply to tissue underlying and surrounding a wound, promoting wound healing.

Additionally, known forms of wound dressing and aspiration and/or irrigation therapy systems often create a wound environment under the backing layer that may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

High frequency vibrational, in particular ultrasonic, energy on and/or in a wound bed surface has been found to result in improved cell proliferation and accelerated growth of tissue whilst resulting in an improved breaking strength of tissue growth that has a strong three-dimensional structure adhering well to and growing from the wound bed, and reduction of wound recurrence.

High frequency vibrational, in particular ultrasonic, energy across the wound bed may also advantageously act against wound bacteria, by breaking up biofilm growth before it develops a strong three-dimensional structure adhering well to and growing from the wound bed, releasing them to be attacked by the body in the wound, and/or breaking up the bacterial cell wall at higher intensities.

It may aid in the debridement of slough, eschar and necrotic tissue growth from the wound.

It is an object of the present invention to provide a system of therapy which i) remove materials deleterious to wound healing from wound exudate, and ii) which creates high frequency vibrational energy, in particular ultrasonic, energy on and/or in a wound bed surface.

The application of high frequency vibrational energy is equally applicable to both sequential systems (i.e., empty/fill cycles) or simultaneous irrigation/aspiration systems. Although it is generally preferred to use a simultaneous system, there may be circumstances where a sequential system is preferred, e.g. due to cost.

According to a first aspect of the present invention there is provided an apparatus for aspirating, irrigating and/or cleansing wounds, comprising a) a fluid flow path, comprising a conformable wound dressing, having a backing layer which is capable of forming a relatively fluid-tight seal or closure over a wound and at least one pipe, which passes through and/or under the wound-facing face to allow irrigation and/or aspiration of the wound, wherein the point at which the or each inlet pipe and the or each outlet pipe passes through and/or under the wound-facing face forming a relatively fluid tight seal or closure over the wound; b) a fluid reservoir connected by a fluid supply tube to the at least one pipe; c) at least one device for moving fluid through the wound dressing; characterized in that it comprises d) means for applying high frequency vibrational, in particular ultrasonic, energy to the wound bed.

Generally it is preferred that the apparatus has at least one inlet pipe for connection to a fluid supply tube to allow irrigation and at least one outlet pipe for connection to a fluid offtake tube to allow aspiration, each of which passes through and/or under the wound-facing face.

Such an embodiment is suitable for both sequential and simultaneous systems, whereas a single pipe system is only suitable for sequential fill/empty cycles.

In one embodiment the present invention provides means for providing simultaneous irrigation and aspiration of the wound, such that fluid may be supplied to fill the flow path from the fluid reservoir via the fluid supply tube (optionally via means for supply flow regulation) while fluid is aspirated by a device through the fluid offtake tube (optionally or as necessary via means for aspirate flow regulation).

Such an embodiment is particularly suitable for simultaneous irrigation and aspiration and thus forms a preferred embodiment by the present invention.

Where any pipe is described in connection with the apparatus as being connected or for connection to a (mating end of a) tube, e.g. a, fluid supply tube or fluid offtake tube, the pipe and the tube may form a single integer in the flow path through which fluid passes.

The means for applying high frequency vibrational, in particular ultrasonic, energy to the wound bed via the irrigant fluid and/or wound exudate may be an high frequency vibrational, in particular ultrasonic, sonode and/or a component of the apparatus flow path connected to a sonode, the sonic conductivity of which is sufficient for it to function as an high frequency vibrational, in particular ultrasonic, conductor.

The source of the ultrasound field may be integral with the sonode, or it may be connected to it by means for an high frequency vibrational, in particular ultrasonic, connection, typically a sonically insulated but conductive waveguide.

The desired or optimum intensities and frequencies of such ultrasound across the wound bed for the stimulation of the healing of wounds will substantially determine a) the position along the apparatus flow path or the component of the apparatus flow path where the means for applying high frequency vibrational, in particular ultrasonic, energy to the wound bed and/or conductively heated component of the apparatus flow path is mounted relative to the dressing; b) the flow rate of irrigant fluid and/or wound exudate; c) the intensity of ultrasound at the point of supply of energy to apparatus that is necessary given the level of energy loss in the system in which the fluid moves and energy is conducted to the wound; and/or d) the nature of the ultrasound source.

Subject to the above, the means to provide high frequency vibrational energy may be at any convenient or appropriate position or component of the apparatus flow path.

Examples include a means for applying high frequency vibrational, in particular ultrasonic, energy to the wound bed and/or conductively connected component of the apparatus flow path a) mounted distally of the body on, in or inside of the dressing; b) mounted in, on, at or 'near one or more of the fluid inlet pipe(s) and outlet pipe(s) that pass through and/or under the wound-facing face of the backing layer; c) mounted in, on, at or near one or more of the connectors in the tubes that form the flow path of the apparatus; and/or d) mounted in, on, at or near the reservoir.

Often, the level of energy loss in the system in which the fluid moves and energy is conducted to the wound; and/or the nature of the ultrasound source. means that a convenient or appropriate position or component of the apparatus flow path for applying high frequency vibrational, in particular ultrasonic, energy to the wound bed and/or conductively connected component of the apparatus flow path is on, in or inside of the dressing and/or in, on, at or near one or more of the fluid inlet pipe(s) and outlet pipe(s) that pass through and/or under the wound-facing face of its backing layer.

In order to effectively deliver high-frequency vibrational, in particular ultrasonic, energy, as an energy field to the wound bed and/or the fluid thereover, there needs to be a suitably conductive bridge between the wound bed surface and the ultrasound sonode. Water is a good transfer medium of ultrasound, so the presence of a substantially continuous bridge of wound fluid and/or irrigant should provide adequate energy transfer.

Both longitudinal and shear waves generated by a transducer mechanism and/or shear waves generated by such longitudinally propagating waves provide effective healing of wounds.

All these types of waves may propagate directly to the wound. Topically applied longitudinal waves may also be reflected by underlying bone tissue and skin layers and these and shear waves generated by them propagate towards the wound for the healing thereof The transducer should be arranged having an operating surface, with the transducer, disposed substantially adjacent to the wound to emit ultra sound to propagate in the direction of the wound for healing thereof.

As shown in FIG. 14, the transducer 500 may include an axis and a focusing element 502 for focusing the propagation of the ultrasound at a predetermined angle with respect to the axis.

The format of such transducers are described in detail in WO 99/56829, WO 99/48621 and U.S. Pat. No. 5,904,659, all of which are incorporated herein by way of reference.

High frequency vibrational, in particular ultrasonic, energy, as is applied in the invention as an ultrasound field to the wound bed and/or the fluid thereover is characterized by parameters such as intensity, frequency, wave form and whether it is slow-pulsed either regularly or randomly on the overall ultrasound waveform.

Examples of suitable intensities of ultrasound applied include a spatial peak temporal average acoustic intensity between 5-100 mW/cm$^2$, e.g. 10 to 75 mW/cm$^2$, such as 30 to 50 mW/cm$^2$. When the ultrasound is slow-pulsed, this allows higher peak intensities.

Higher intensity ultrasound is more for hospital use, where relatively high intensities and/or pulsing can only be used safely with professional supervision, or for field hospital use.

Examples of suitable frequencies of ultrasound across the wound bed for the stimulation of the healing of wounds include in general an ultrasound carrier frequency between 20 kHz and 10 MHz, such as 60 kHz to 5 MHz, such as 200 kHz to 3 MHz.

It will be understood that where any layers of dressing or apparatus lie between the source of ultrasound and the wound bed, it may be necessary to increase the intensity and/or other properties of the ultrasound to take account of attenuation or other factors which affect the delivery of ultrasound energy to the wound bed.

Examples of suitable waveforms of ultrasound across the wound bed for the stimulation of the healing of such wounds include those described in detail in WO 99/56829, WO 99/48621 and U.S. Pat. No. 5,904,659, all of which are incorporated herein by way of reference optionally slow-pulsed either regularly or randomly on the overall ultrasound waveform.

These may be optionally slow-pulsed either regularly or randomly on the overall vibrational waveform with a relatively low-frequency modulating signal.

Examples of suitable pulsing of ultrasound on/across the wound bed for the stimulation of the healing of wounds include pulsing at low frequencies such as 5 Hz to 10 kHz.

Application may be made continuously or intermittently, for example 1-4 times daily for a period of 20 minutes per application.

As noted above, the apparatus for irrigating, supplying high frequency vibrational, in particular ultrasonic, energy to and/or cleansing wounds of the present invention is characterized in that it comprises at least one sonode for applying a vibrational field to the wound bed and/or the fluid thereover.

The source of the sound field may be connected to the sonode by means for an high frequency vibrational, in particular ultrasonic, connection, typically a sonically insulated but conductive waveguide, or it may be integral with or comprise it In the former case, the source may be of any conventional type, e.g., in the case of ultrasound, a piezoelectric transducer; or others described in detail in WO 99/56829, WO 99/48621 and U.S. Pat. No. 5,904,659, all of which are incorporated herein by way of reference.

Suitable materials for the sonode include materials that do not absorb high frequency vibrational (e.g. ultrasonic) energy, such as an Exogen™ device (produced by Smith & Nephew). Suitable materials for the waveguides include ultrasound-conductive materials such as those described in detail in WO 99/56829, WO 99/48621 and U.S. Pat. No. 5,904,659, all of which are incorporated herein by way of reference. Examples of instances where the sonode effectively is or is integral with the ultrasonic source, include a piezoelectric transducer directly attached to or integral with a component of the apparatus flow path.

Suitable materials for such a piezoelectric transducing sonode include those described in detail in WO 99/56829, WO 99/48621 and U.S. Pat. No. 5,904,659, all of which are incorporated herein by way of reference.

These include synthetic polymeric materials such as certain halogenated polyolefins, such as fluorinated olefin polymers and copolymers, such as polyvinylidene fluoride and copolymers thereof.

Examples of suitable materials also include thermoplastics, and elastomers and elastomer blends, having for example particulate piezoelectric dispersed through it, such as the certain halogenated polyolefins, such as fluorinated olefin polymers and copolymers, such as polyvinylidene fluoride and copolymers thereof mentioned above; and certain minerals, such as quartz.

Examples of suitable such thermoplastics materials and elastomers and elastomer blends include synthetic polymeric materials that do not absorb aqueous fluids, such as polyolefins, such as polyethylene e.g. high-density polyethylene,—polypropylene, copolymers thereof, for example with vinyl acetate and polyvinyl alcohol, and mixtures thereof; polysiloxanes; polyesters, such as polycarbonates; polyamides, e.g. nylon 6-6 and 6-10; and hydrophobic polyurethanes.

They may be hydrophilic, and thus also include hydrophilic polyurethanes. They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Where the source is or includes a piezoelectric transducer, it will be electrically stimulated to change shape repeatedly as appropriate or desired at ultrasonic frequencies by an ultrasonic frequency electrical signal generator run at the appropriate frequencies.

The sonode or sonode-transducer may be mounted at any convenient or appropriate position or component of the apparatus flow path. Typically, however, as noted above, it is a) mounted distally of the body on, in or inside of the dressing; and/or b) mounted in, on, at or near one or more of the fluid inlet pipe(s) and outlet pipe(s) that pass through and/or under the wound-facing face of the backing layer.

It will be so positioned as to apply an ultrasound field to the fluid across the wound bed and/or to be in contact with the wound bed and/or the surrounding surfaces of the body. It may be more convenient if the sonode or sonode-transducer is outside the dressing, since otherwise it requires that a waveguide or electric leads will pass through and/or under the wound-facing face of the backing layer, and the point at which it passes or they through and/or under the wound-facing face must form a relatively fluid-tight seal or closure over the wound.

Where the sonode or sonode-transducer is mounted on the dressing, e.g. the backing layer, the wound dressing may then effectively be capable of being electrically stimulated to change shape repeatedly as appropriate or desired at high frequency vibrational, in particular ultrasonic, frequencies.

In all relevant embodiments of the present apparatus where the sonode or sonode-transducer is mounted distally of the body on, in or inside of the dressing, it will often be at or near the center of the dressing backing layer. It may be attached to or integral with it.

Where the sonode-transducer is mounted distally of the body on, in or inside of the dressing, it may be in the form of a relatively laminar integer, for example a discoidal pellet, foil, film, sheet or membrane.

It may be mounted to be clear of or surround one or more of the fluid inlet pipe(s) and outlet pipe(s) that pass through and/or under the wound-facing face of the backing layer.

The sonode or sonode-transducer may be attached, as appropriate by heat-sealing or by adhesive, or it may be a push, slide, snap or twist-lock fit.

For example, in the former case, a sonode-transducer such as a film, sheet or membrane of or comprising a piezoelectric transducing polyolefin, such as polyvinylidene fluoride and copolymers thereof, may be attached, e.g. by an adhesive, in particular a curable adhesive, coextrusion or heat lamination to the dressing.

It may be mounted distally on the backing layer to be clear of or surround one or more of the fluid inlet pipe(s) and outlet pipe(s) that pass through and/or under the wound-facing face of the backing layer.

Alternatively, it may be mounted proximally on the backing layer to be clear of, surround or pass across one or more of the fluid inlet pipe(s) and outlet pipe(s) that pass through and/or under the wound-facing face of the backing layer.

In the last case, it will have to be mounted on relatively stiff but still conformable, proximally projecting struts, supports, braces or stays, or on a similar proximally projecting boss to permit ingress or egress of fluid as appropriate.

Where the sonode or sonode-transducer is attached as a push, slide, snap or twist-lock fit, it may for example be mounted distally or proximally on the backing layer clear of the fluid inlet pipe(s) and outlet pipe(s) that pass through and/or under the wound-facing face of the backing layer, as a push fit in a (respectively) distally or proximally projecting recessed boss.

For example, a sonode such as an Exogen™ device may be a push fit in a distally projecting recessed boss on the distal backing layer surface.

The sonode or is then connected ultrasonically to the dressing backing sheet by a layer of ultrasound coupling material, e.g. a coupling gel, which is needed to transmit the energy to the irrigant and/or exudate under the wound-facing face of the wound dressing.

A sonode-transducer, for example a disc, film, sheet or membrane, of or comprising a piezoelectric, such as polyvinylidene fluoride and copolymers thereof mentioned above, may be mounted at any convenient or appropriate position, in or inside of the dressing, as a push fit in a proximally projecting recessed boss.

Such a sonode/transducer does not need to be connected ultrasonically to the dressing backing sheet by a layer of ultrasound coupling material, e.g. the adhesive or by a coupling gel, which is needed to transmit the energy to the irrigant and/or exudate under the wound-facing face of the wound dressing.

However, it requires that electric leads pass through and/or under the wound-facing face of the backing layer, but the point at which they pass through the wound-facing face is not in contact with fluid, so that the closure over the wound is not prejudiced.

As noted above, the sonode or sonode-transducer may be mounted in, on, at or near one or more of the fluid inlet pipe(s) and outlet pipe(s) that pass through and/or under the wound-facing face of the backing layer, In such case, the nature of the sonode or sonode-transducer, and the manner and position in which it may be mounted are similar to the those in the case of mounting in or on the dressing mutatis mutandis.

Mounting in, on, at or near one or more of the fluid inlet pipe(s) and outlet pipe(s) may however be less preferred than mounting on the backing layer at any convenient or appropriate position, since, because of the orientation of the pipes, it may be less easy to direct the high-frequency vibrational or ultrasonic energy sufficiently to achieve adequate therapeutic intensities across the wound bed for the stimulation of the healing of wounds.

Suitable dressings are depicted and described in more detail hereinafter.

Where the present invention involves simultaneous irrigation/aspiration it provides several further advantages.

One is that application of an irrigant to a wound under simultaneous aspiration creates a wound environment that is exposed to the continuous beneficial effects of both aspects of the therapy for wound healing, as opposed to the sequential intermittent application of irrigant flow and aspiration in known aspirating and/or irrigating apparatus. The latter result in less than optimum performance of the body's own tissue healing processes, and slower healing and/or weaker tissue growth that does not have a strong three-dimensional structure adhering well to and growing from the wound bed. This is a significant disadvantage, in particular in chronic wounds.

Such a system is particular suited for removing materials deleterious to wound healing with the wound exudate, reducing bacterial load, combating peri-wound oedema and encouraging the formation of wound bed granulation tissue.

Preferred embodiments of the apparatus of the present invention for aspirating, irrigating and/or cleansing chronic wounds apply a milder negative pressure than in conventional negative pressure therapy (which is too aggressive for the fragile tissues of many such wounds). This leads to increased patient comfort, and lessens the risk of inflammation of the wound.

The removal of wound exudate in a given time period of application of the simultaneous irrigate and/or aspirate therapy will normally be more effective and/or faster than with a conventional sequential intermittent aspiration and/or irrigation therapy.

Even more desirably, since simultaneous aspiration and irrigation is applied to the wound, wound exudate and materials deleterious to wound healing (such as bacteria and debris, and iron II and iron Ill and for chronic wounds proteases) will not pool on the wound bed and hinder wound healing, especially in a highly exuding wound. This is especially important in chronic wounds.

The resulting mixed exudate-irrigant fluid will usually be of relatively lower viscosity.

Because simultaneous aspiration and irrigation of the wound provides continuous removal at a constant relatively high speed, the fluid does not have to be accelerated cyclically from rest, and will be easier to shift than with known forms of aspiration and/or irrigation therapy systems with a conventional sequential aspirate-irrigate-dwell cycle. This will thus exert a greater net effect on the removal of adherent bacteria and debris.

This is especially the case in those embodiments of the apparatus of the present invention for aspirating, irrigating and/or cleansing wounds where there is an inlet manifold (as described in further detail hereinafter) that covers and contacts a significant area, preferably most, of the wound bed with openings that deliver the fluid directly to the wound bed over an extended area.

It will be seen that the balance of fluid between fluid aspirated from the wound and irrigant supplied to the wound from the irrigant reservoir may provide a predetermined steady state concentration equilibrium of materials beneficial in promoting wound healing over the wound bed. Simultaneous aspiration of wound fluid and irrigation at a controlled flow rate aids in the attainment and maintenance of this equilibrium.

The apparatus for irrigating and/or aspirating wounds of the present invention may be used cyclically and/or with reversal of flow.

Preferably the present apparatus for aspirating, irrigating and/or cleansing wounds is a conventionally automated, programmable system which can cleanse the wound with minimal supervision.

The means for providing. simultaneous aspiration and irrigation of the wound often comprises a (first) device for moving fluid through the wound applied to fluid downstream of and away from the wound dressing in combination with at least one of a second device for moving fluid through the wound applied to the irrigant in the fluid supply tube upstream of and towards the wound dressing; means for aspirate flow regulation, connected to a fluid offtake tube, and means for supply flow regulation, connected to a fluid supply tube.

The (first) device will apply negative pressure (i.e. below-atmospheric pressure or vacuum) to the wound bed. It may be applied to the aspirate in the fluid offtake tube downstream of and away from the wound dressing.

Alternatively or additionally, where appropriate, the aspirate in the fluid offtake tube downstream of the wound dressing may be aspirated into a collection vessel, and the first device may act on fluid such as air from the collection vessel. This prevents contact of the device with the aspirate.

The (first) device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve.

Alternatively, where appropriate the (first) device for moving fluid through the wound may be a variable-throughput device, such as a variable-speed pump, downstream of the wound dressing, thus effectively forming a combination of a (first) device for moving fluid through the wound with means for aspirate flow regulation and/or means for supply flow regulation in a single integer.

The (first) device for moving fluid through the wound will often be a pump of any of the types set out below, or a piped supply of vacuum, applied to fluid downstream of and away from the wound dressing. In the case of any pump it may be a fixed-speed pump, with (as above) a discrete means for aspirate flow regulation, connected to a fluid offtake tube, and/or means for supply flow regulation, connected to a fluid supply tube, in each case, e.g. a regulator, such as a rotary valve. Alternatively, where appropriate the pump may be a variable-throughput or variable-speed pump.

The following types of pump may be used as the (first) device:

Reciprocating Pumps, such as Piston Pumps—where pistons pump fluids through check valves, in particular for positive and/or negative pressure on the wound bed; and Diaphragm Pumps—where pulsations of one or two flexible diaphragms displace liquid with check valves and Rotary Pumps, such as:

Progressing Cavity Pumps with a cooperating screw rotor and stator, in particular for higher-viscosity and particulate filled exudate; and Vacuum Pumps with pressure regulators.

The (first) device may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as a piezoelectric transducer, a core of a solenoid or a ferromagnetic integer and coil in which the direction of current flow alternates, a rotary cam and follower, and so on.

Where any second device is applied to the fluid in the fluid supply tube upstream of and towards the wound dressing, it will usually apply positive pressure (i.e. above-atmospheric pressure) to the wound bed.

As with the (first) device, it may be a fixed-throughput device, such as a fixed-speed pump, which will usually require a discrete means for supply flow regulation, connected to a fluid supply tube, e.g. a regulator, such as a rotary valve.

Alternatively, where appropriate the second device for moving irrigant fluid to the wound may be a variable-throughput device, such as a variable speed pump, upstream of the wound dressing, thus effectively forming a combination of a second device for moving fluid through the wound with means for supply flow regulation in a single integer.

The second device for moving fluid through the wound will often be a pump of any of the following types applied to the irrigant in the fluid supply tube upstream of and towards the wound dressing. It may be a fixed-speed pump, with (as above) a discrete means for supply flow regulation, connected to a fluid supply tube, e.g. a regulator, such as a rotary valve. Alternatively, where appropriate the pump may be a variable-throughput or variable-speed pump.

The following types of pump may be used as the second device:

Reciprocating Pumps, such as
  Shuttle Pumps—with an oscillating shuttle mechanism to move fluids at rates from 2 to 50 ml per minute and
Rotary Pumps, such as:
  Centrifugal Pumps
  Flexible Impeller
Pumps—where elastomeric impeller traps fluid between impeller blades and a moulded housing that sweeps fluid through the pump housing.
Peristaltic Pumps—with peripheral rollers on rotor arms acting on a flexible fluid aspiration tube to urge fluid current flow in the tube in the direction of the rotor.
Rotary Vane Pumps—with rotating vaned disk attached to a drive shaft moving fluid without pulsation as it spins. The outlet can be restricted without damaging the pump.

The second device may be a peristaltic pump, e.g. preferably a small portable peristaltic pump. This is a preferred type of pump, in order in particular to reduce or eliminate contact of internal surfaces and moving parts of the pump with irrigant, and for ease of cleaning.

Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

Each such pump of any these types may also suitably be one that is capable of pulsed, continuous, variable and/or automated and/or programmable fluid movement. Less usually and less preferably, each such pump of any these types will be reversible.

As above, the means for supply flow regulation may be a regulator, such as a rotary valve. This is connected between two parts of a fluid supply tube, such that the desired supply flow regulation is achieved.

If there are two or more inlet pipes, these may be connected to a single fluid supply tube with a single regulator, or to first, second, etc. fluid supply tubes, respectively having a first regulator, a second regulator, etc., e.g. a valve or other control device for admitting fluids into the wound.

As above, the means for aspirate flow regulation may be similarly provided in a form in which concomitant aspirate flow regulation is possible. It may be a regulator, such as a valve or other control device, e.g. a rotary valve.

Multiple offtake tubes may be similarly provided with single or multiple regulators, all for aspiration of fluids from the apparatus, e.g. to a aspirate collection vessel, such as a collection bag.

If there is no second device for moving fluid through the wound applied to the irrigant in the fluid supply tube upstream of and towards the wound dressing, it is only possible to apply a negative pressure to the wound, by means of the device for moving fluid through the wound applied to the aspirate in the fluid offtake tube downstream of and away from the wound dressing.

Operation may e.g. be carried out at a negative pressure of up to 50% atm., typically at a low negative pressure of up to 20% atm., more usually up to 10% atm. at the wound, as is described hereinafter.

Examples of suitable and preferred (first) devices include those types of pump that are so described hereinbefore in relation to the first device. This may be a diaphragm pump, e.g. preferably a small portable diaphragm pump. This is a preferred type of pump, in order in particular to reduce or eliminate contact of internal surfaces and moving parts of the pump with (chronic) wound exudate, and for ease of cleaning.

Alternatively, if it is desired to apply a net positive pressure to the wound, the means for providing simultaneous aspiration and irrigation of the wound must comprise not only a first device for moving fluid through the wound applied to the aspirate in the fluid offtake tube downstream of and away from the wound dressing, but also a second device for moving fluid through the wound applied to the irrigant in the fluid supply tube upstream of and towards the wound dressing.

Operation may then e.g. be carried out at a positive pressure of up to 50% atm., typically at a low positive pressure of up to 20% atm., more usually up to 10% atm. at the wound, as is described hereinafter.

Examples of suitable and preferred first devices include those types of pump that are so described hereinbefore in relation to the first device. This may be a diaphragm pump, e.g. preferably a small portable diaphragm pump.

This is a preferred type of pump, in order in particular to reduce or eliminate contact of internal surfaces and moving parts of the pump with (chronic) wound exudate, and for ease of cleaning.

Examples of suitable and preferred second devices include those types of pump that are so described hereinbefore in relation to the second device. This may be a peristaltic pump, e.g. a miniature peristaltic pump.

This is a preferred type of pump, in order to eliminate contact of internal surfaces and moving parts of the pump with irrigant in the fluid supply tube upstream of and towards the wound dressing, and for ease of cleaning.

It is of course equally possible to apply a negative pressure to the wound, by means of such a combination of a first device for moving fluid through the wound applied to the aspirate in the fluid offtake tube downstream of and away from the wound dressing, and a second device for moving fluid through the wound applied to the irrigant in the fluid supply tube upstream of and towards the wound dressing; optionally with means for supply flow regulation, connected to a fluid supply tube; and/or means for aspirate flow regulation, connected to a fluid offtake tube.

Indeed, as noted below in this regard, preferred embodiments of the apparatus of this first aspect of the present invention for aspirating, irrigating and/or cleansing chronic wounds that apply a negative pressure include such types of combination of; a first device, e.g. a diaphragm pump, e.g. preferably a small portable diaphragm pump, and a second device, e.g. a peristaltic pump, preferably a miniature peristaltic pump, As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integer. The higher end of the ranges of % positive and negative pressure noted above—are potentially more suitable for hospital use, where they may only be used safely under professional supervision.

The lower end is potentially more suitable for home use, where relatively high % positive and negative pressures cannot be used safely without professional supervision, or for field hospital use.

In each case, the pressure on the wound may be held constant throughout the desired length of therapy, or may be varied cyclically in a desired positive or negative pressure regime.

As noted above, when it is desired to apply a negative pressure to the wound, it is preferred that the means for providing simultaneous aspiration and irrigation of the wound comprise not only a (first) device for moving fluid through the wound applied to the aspirate in the fluid offtake tube downstream of and away from the wound dressing, but also a second device for moving fluid through the wound applied to the irrigant in the fluid supply tube upstream of and towards the wound dressing.

Accordingly, one embodiment of the apparatus for irrigating, cleansing and/or aspirating wounds of the present invention is characterized in the means for providing simultaneous aspiration and irrigation of the wound comprises: a (first) device for moving fluid through the wound applied to fluid downstream of and away from the wound dressing, and a second device for moving fluid through the wound applied to the irrigant in the fluid supply tube upstream of and towards the wound dressing; in combination with at least one of means for supply flow regulation, connected to a fluid supply tube; and means for aspirate flow regulation, connected to a fluid offtake tube.

As noted above, either of the first device and the second device may be a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or a variable-throughput device, such as a variable-speed pump, downstream of the wound dressing, thus effectively forming a combination of a (first) device for moving fluid through the wound with means for aspirate flow regulation and/or means for supply flow regulation in a single integer.

This combination of a) a device for moving fluid through the wound applied to the aspirate in the fluid offtake tube downstream of and away from the wound dressing, and b) a device for moving fluid through the wound applied to the fluid in the fluid supply tube upstream of and towards the wound dressing, may be used to apply an overall positive or negative, or even zero pressure to the wound.

At least one body in the flow path to, over and from the wound bed should have sufficient resilience against the pressure to allow any significant compression or decompression of the fluid occur.

Thus, examples of suitable bodies include those which are or are defined by a film, sheet or membrane, such as inlet or offtake and/or tubes and structures such as bags, chambers and pouches, filled with irrigant fluid, and e.g. the backing layer of the wound dressing, made of elastically resilient thermoplastic materials.

It will be seen that the balance of fluid between aspirated fluid from the wound and irrigant supplied to the wound from the fluid reservoir will thus be largely determined by a means for providing simultaneous aspiration and irrigation of the wound which is a system comprising: a) means for aspirate flow regulation and/or a device for moving fluid through the wound applied to fluid downstream of and away from the wound dressing, and b) means for supply flow regulation and/or a device for moving fluid through the wound applied to the fluid in the fluid supply tube upstream of and towards the wound dressing.

The same means may be used to apply an overall positive or negative, or even neutral pressure to the wound.

The appropriate flow rate through the supply tube will depend on a number of factors, such as:

the viscosity and consistency of each of the irrigant, exudate and mixed exudate-irrigant fluid, and any changes as the wound heals;

the level of negative pressure on the wound bed, whether the irrigant in the fluid supply tube upstream of and into the wound dressing is under positive pressure, and the level of such pressure;

the level of any pressure drop between the irrigant in the fluid supply tube upstream of the wound dressing and the wound bed, such as across a porous element, e.g. a membrane wound contact layer on the lower surface of an inlet manifold that delivers the fluid directly to the wound bed;

means for supply flow regulation;

and/or a second device for moving fluid through the wound applied to the fluid in the fluid supply tube upstream of and towards the wound dressing;

the depth and/or capacity of the wound and the power consumption needed for a given desired fluid volume flow rate of irrigant and/or wound exudate through the wound.

The dressing may comprise an inlet manifold (as described in further detail hereinafter) that generally covers and contacts a significant area, preferably most, of the wound bed with openings that deliver the fluid directly to the wound bed over an extended area, in the form of one or more inflatable hollow bodies defined by a film sheet or membrane. The (usually small) positive pressure above atmospheric from the irrigation device when both devices are running together should be sufficient to inflate the manifold.

The desired fluid volume flow rate of irrigant and/or wound exudate is preferably that for optimum performance of the wound healing process.

The flow rate will usually be in the range of 1 to 1500 ml/hr, such as 5 to 1000 ml/hr, e.g. 15 to 300 ml/hr, such as 35 to 200 ml/hr through the supply tube. The flow rate through the wound may be held constant throughout the desired length of therapy, or may be varied cyclically in a desired flow rate regime.

In practice, the offtake rate of flow of total irrigant and/or wound exudate will generally be of the order of 1 to 2000, e.g. 35 to 300 ml/24 hr/cm$^2$, where the cm$^2$ refers to the wound area, depending on whether the wound is in a highly exuding state.

In practice, the rate of exudate flow is typically only of the order of up to 75 microlitres/cm$^2$/hr (where cm$^2$ refers to the wound area), and the fluid can be highly mobile or not, depending on the level of proteases present). Exudate levels drop and consistency changes as the wound heals, e.g. to a level for the same wound that equates to 12.5-25 microlitres/cm$^2$/hr.

It will be apparent that the aspirated fluid from the wound will typically contain a preponderance of irrigant from the fluid reservoir over wound exudate.

The necessary adjustments to maintain the desired balance of fluid by means of a) the means for aspirate flow regulation and/or downstream device, and b) the means for supply flow regulation and/or upstream device for moving fluid will be apparent to the skilled person, bearing in mind that, as noted above, either of the first device and the second device may be:
- a fixed-throughput device, such as a fixed-speed pump, which will usually require a discrete means for aspirate flow regulation, connected to a fluid offtake tube, and/or means for supply flow regulation, connected to a fluid supply tube, in each case, e.g. a regulator, such as a rotary valve, or
- a variable-throughput device, such as a variable-speed pump, downstream of the wound dressing, thus effectively forming a combination of a (first) device for moving fluid through the wound with means for aspirate flow regulation and/or means for supply flow regulation in a single integer.

The type and/or capacity of a suitable second device will be largely determined by a) the appropriate or desired fluid volume flow rate of irrigant and/or wound exudate from the wound, and b) whether it is appropriate or desired to apply a positive or negative pressure to the wound bed, and the level of such pressure to the wound bed for optimum performance of the wound healing process, and by factors such as portability, power consumption and isolation from contamination.

As noted above, when it is desired to apply a negative pressure to the wound with the apparatus of the present invention for aspirating, irrigating and/or cleansing wounds to provide simultaneous aspiration and irrigation of the wound, the means for providing simultaneous aspiration and irrigation of the wound may comprise a single device for moving fluid through the wound applied to the aspirate in the fluid offtake tube downstream of and away from the wound dressing or in combination with at least one of means for supply flow regulation, connected to a fluid supply tube, and means for aspirate flow regulation, connected to a fluid offtake tube.

As noted above, the device may be a fixed-throughput device, or a variable throughput device.

It should be noted that such an apparatus as described above will be generally suitable for sequential irrigation/aspiration.

In a further aspect the present invention provides a method of operation of an apparatus for aspirating, irrigating and/or cleansing wounds, said method comprising the steps of: a) providing an apparatus as set out above b) applying the wound dressing to the wound c) conforming the backing layer of the wound dressing to the shape of the bodily part in which the wound is to form a relatively fluid tight seal or closure; d) activating at least one device for moving fluid through the wound dressing to the wound and/or from the wound to course irrigant to move to the wound; e) activating means for applying high frequency vibrational energy to the wound bed.

In a preferred embodiment the apparatus has at least one inlet pipe and at least one outlet pipe, each of which passes through and/or under the wound-facing face. Such an embodiment allows for a method of simultaneous and/or sequential irrigation/aspiration of the wound. In such an embodiment step d) of the method comprises activating at least one device for moving through the wound dressing to move fluid (irrigant) through the at least one inlet and to move fluid (aspirate) out of the at least one output pipe.

In a preferred embodiment the irrigant is moved to the wound via the outlet pipe and the aspirate removed via the outlet pipe. simultaneously, i.e. simultaneous aspiration/irrigation. This may be carried out for substantially the entirety of the treatment of the wound, or alternatively for portions of the treatment as desired.

Such an embodiment is also suitable for sequential (fill/empty) operation, and thus a method wherein sequential operation is carried out forms an alternative embodiment of the invention. In such an embodiment irrigation would be ceased by ceasing the device moving fluid through the at least one inlet and activating a device to move fluid from the wound through the outlet.

Suitable flow rates, parameters for operation of the means for applying stress and for operation of the apparatus in general are set out above. Further details are given below.

The operation of a typical apparatus of this type for simultaneous aspiration and irrigation of a wound at a low negative pressure of up to 20% atm., more usually up to 10% atm. at the wound, with one pump may involve the following. As mentioned previously the application of negative pressure has beneficial effects in wound healing.

Before starting the apparatus of this first aspect of the present invention for aspirating, irrigating and/or cleansing wounds, the backing layer of the wound dressing is applied over the wound and conformed to the shape of the bodily part in which the wound is to form a relatively fluid-tight seal or closure.

The means for supply flow regulation, connected to a fluid supply tube, such as a regulator, such as a rotary valve, is usually closed, and the means for aspirate flow regulation (if any), connected to a fluid offtake tube, is opened.

The aspiration pump is started and run to give a negative pressure of up to 50% atm., more usually up to 20% atm., e.g. up to 10% atm. to be applied to the interior of the dressing and the wound.

The means for fluid supply regulation is opened and is then adjusted, and/or where the aspiration pump is a variable-speed pump, downstream of the wound dressing, that is adjusted, to maintain the desired balance of fluid at a controlled nominal flow rate and to maintain the desired negative pressure in the interior of the wound dressing.

The means for applying high frequency vibrational energy to the wound bed is then activated. Further details of this means and its operation are given above. The means may be activated continuously or intermitted as desired.

The apparatus is then run for the desired length of therapy and with the desired negative pressure regime and with application of the high frequency vibrational energy regime as desired.

After this period, the aspiration pump is stopped.

The operation of a typical apparatus for simultaneous aspiration and irrigation of a wound at a low negative pressure of up to 20% atm., more usually up to 10% atm. at the wound, with two pumps may involve the following steps.

The necessary changes where the mode of operation is at a net positive pressure of e.g. up to 15% atm., more usually up to 10% atm. at the wound will be apparent to the skilled person.

Such a typical apparatus for simultaneous aspiration and irrigation of a wound at a low negative pressure of up to 20% atm., more usually up to 10% atm. at the wound comprises means for. Providing simultaneous aspiration and irrigation of the wound which is a combination of a) a first device for moving fluid through the wound applied to the aspirate in the fluid offtake tube downstream of and away from the wound dressing, with optional means for aspirate flow regulation, connected to a fluid offtake tube: and b) a second device for moving fluid through the wound applied to the irrigant in the fluid supply tube upstream of and towards the wound dressing, with optional means for supply flow regulation, connected to a fluid supply tube.

As noted above, either device may be a fixed-throughput device or variable throughput device.

Before starting the apparatus of this first aspect of the present invention for aspirating, irrigating and/or cleansing wounds, the backing layer of the wound dressing is applied over the wound and conformed to the shape of the bodily part in which the wound is to form a relatively fluid-tight seal or closure.

Any means for supply flow regulation, connected to a fluid supply tube, such as a regulator; such as a rotary valve, is usually closed, and any means for aspirate flow regulation, connected to a fluid offtake tube, is opened.

The aspiration pump is started and run to apply a negative pressure of up to 50% atm., more usually up to 20% atm., e.g. up to 10% atm., to the interior of the dressing and the wound.

The irrigation pump is then started, so that both pumps are running together, and any means for supply flow regulation is opened.

The irrigation pump flow rate and any means for fluid supply regulation are then adjusted and/or where the aspiration pump and/or the irrigation pump is a variable-speed pump, either or both is/are is adjusted, to maintain the desired balance of fluid at a controlled nominal flow rate and to maintain the desired negative pressure in the interior of the wound dressing.

The means for applying high frequency vibrational energy is then activated, as discussed previously.

The apparatus is then run for the desired length of therapy and with the desired pressure regime and high frequency vibrational energy regime.

After this period, the irrigation pump is stopped, shortly followed by the aspiration pump.

In all embodiments of the apparatus of this first aspect of the present invention for aspirating, irrigating and/or cleansing wounds, a particular advantage is the tendency of the wound dressing to conform to the shape of the bodily part to which it is applied.

The term 'relatively fluid-tight seal or closure' is used herein to indicate one which is fluid- and microbe-impermeable and permits a positive or negative pressure of up to 50% atm., more usually up to 20% atm., e.g. up to 10% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high density polyethylene, polypropylene, copolymers thereof, for example with vinyl acetate and polyvinyl alcohol, and mixtures thereof; polysiloxanes; polyesters, such as polycarbonates; polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound. This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a. flange or lip extending around the proximal face of the backing layer, of a transparent or translucent material (for which it will be understood that materials that are listed above are amongst those that are suitable). This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings. Where a vacuum, is applied to hold the wound dressing in place in a fluid tight seal around the periphery of the wound-facing face of the wound dressing, the wound dressing may be provided with a silicone flange or lip to seal the dressing around the wound. This removes the need for adhesives and associated trauma to the patient's skin. Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide securing means for forming and maintaining such a seal or closure over the wound against such positive pressure on the wound, to act at peripheral points for this purpose. Examples of such securing means include light switchable adhesives, as above, to secure the dressing in place to prevent leakage. Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such securing means include adhesive (e.g. with pressure-sensitive adhesive) and non-adhesive, and elastic and nonelastic straps, bands, loops, strips, ties, bandages, e.g. compression bandages, sheets, covers, sleeves, jackets, sheathes, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheathes, wraps, stockings and hose that are a compressive fit over a limb wound to apply suitable pressure to it when the therapy is applied in this way.

Such securing means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such securing means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The securing means and the dressing may be separate structures, permanently unattached to each other.

In a more suitable layout for higher positive pressures on the wound, a stiff flange or lip extends around the periphery of the proximal face of the backing layer of the wound dressing as hereinbefore defined. The flange or lip is concave on its proximal face to define a peripheral channel or conduit. It has a suction outlet that passes through the flange or lip to communicate with the channel or conduit and may be connected to a device for applying a vacuum, such as a pump or a piped supply of vacuum.

The backing layer may be integral with or attached, for example by heat sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound. The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of a fluid tube and/or fluid supply tube (optionally or as necessary via means for forming a tube, pipe or hose, or nozzle, hole, opening, orifice, luer, slot or port for connection as a male member respectively to a mating end of a fluid tube and/or fluid supply tube (optionally or as necessary via means for supply flow regulation) or a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The or each pipe will generally pass through, rather than under the backing layer. In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer.

Where a simple pipe is used to supply the irrigant to the wound, this may not provide a system to distribute irrigant over a sufficient functional surface area to irrigate the wound at a practical rate to be suitable for use, in particular in chronic wound aspiration and irrigation, which may contain relatively high concentrations of materials that are deleterious to wound healing.

It may be advantageous to provide a system where wound irrigant may be distributed more evenly, or pass in a more convoluted path under the dressing over the wound bed.

Accordingly, one form of the dressing is provided with a 'tree' form of pipes, tubes or tubules that radiate from an inlet manifold to the wound bed to end in apertures and deliver the aspirating fluid directly to the wound bed via the apertures. Similarly, there is optionally an outlet manifold from which tubules radiate and run to the wound bed to end in openings and collect the fluid directly from the wound bed.

The pipes, etc. may radiate regularly or irregularly through the wound in use, respectively from the inlet or outlet manifold, although regularly may be preferred. A more suitable layout for deeper wounds is one in which the pipes, etc. radiate hemispherically and concentrically, to the wound bed.

For shallower wounds, examples of suitable forms of such layout of the pipes, etc. include ones in which the pipes, etc. radiate in a flattened hemiellipsoid and concentrically, to the wound bed. Other suitable forms of layout of the pipes, etc. include one which have pipes, tubes or tubules extending from the inlet pipe(s) and/or outlet pipe(s) at the point at which they pass through and/or under the wound-facing face of the backing layer to run over the wound bed. These may have a blind bore with perforations, apertures, holes, openings, orifices, slits or slots along the pipes, etc.

These pipes, etc. then effectively form an inlet pipe manifold that delivers the aspirating fluid directly to the wound bed or outlet pipe or collects the fluid directly from the wound respectively. It does so via the holes, openings, orifices, slits or slots in the tubes, pipes, tubules, etc. over most of the wound bed under the backing layer.

It may be desirable that the tubes, pipes or tubules are resiliently flexible, e.g. elastomeric, and preferably soft, structures with good conformability in the wound and the interior of the wound dressing.

When the therapy is applied in this way, the layout of the tubes, pipes, tubules, etc. may depend on the depth and/or capacity of the wound.

Thus, for shallower wounds, examples of suitable forms of such layout of the tubes, pipes, tubules, etc. include ones that consist essentially of one or more of the tubes, etc. in a spiral.

A more suitable layout for deeper wounds when the therapy is applied in this way may be one which comprises one or more of the tubes, etc. in a helix or spiral helix.

Other suitable layouts for shallower wounds include one which have blindbore, perforated inlet pipe or outlet pipe manifolds that aspirate fluid in the wound when the dressing is in use.

One or both of these may be such a form, the other may be, e.g. one or more straight blind-bore, perforated radial tubes, pipes or nozzles.

A preferred form of inlet pipe (or less usually outlet pipe) manifold that delivers the aspirating fluid directly to the wound bed or collects the fluid directly from the wound respectively is one that comprise one or more conformable hollow bodies defined by a film, sheet or membrane, such as a bag, chamber, pouch or other structure, filled with the irrigant (or less usually) aspirate from the wound, passing through perforations, apertures, holes, openings, orifices, slits or slots in the film, sheet or membrane defining the hollow body or hollow bodies.

These may be of small cross-dimension, so that they may then effectively form microperforations, microapertures or pores in a permeable integer, for example the polymer film, sheet or membrane.

This type of manifold for irrigation (more usually) provides the highest uniformity in the flow distribution of irrigant over the wound at a practical rate to be suitable for use, in particular in chronic wound aspiration and irrigation, and hence to provide a system where materials that are beneficial in promoting wound healing, such as growth factors, cell matrix components, and other physiologically active components of the exudate from a wound, are distributed more evenly under the dressing over the wound bed.

This type of manifold for irrigation (more usually) is noted below with regard to wound fillers under the backing layer, since it is a resiliently flexible, e.g. elastomeric, and soft, structure with good conformability to wound shape. It is urged by its own resilience against the backing layer to apply gentle pressure on the wound bed, and is therefore also capable of acting as a wound filler. The film, sheet or membrane, often has a (generally uniform) thickness similar to that of films or sheets used in conventional wound dressing backing layers.

Another suitable layout is one in which an inlet pipe and/or outlet pipe manifold that delivers the aspirating fluid directly to the wound bed or collects the fluid directly from the wound respectively via inlet and/or outlet tubes, pipes or tubules, and the inlet manifold and/or outlet manifold is formed by slots in layers permanently attached to each other in a stack, and the inlet and/or outlet tubes, pipes or tubules are formed by apertures through layers permanently attached to each other in a stack. (In FIG. 10a there is shown an exploded isometric view of such a stack, which is non-limiting.)

As also mentioned herein, the backing layer that is applied may be any that is appropriate to the present system of therapy and permits a positive or negative pressure of up to 50% atm., more usually up to 25% atm. to be applied to the wound.

It is thus often a microbe-impermeable film, sheet or membrane, which is substantially flat, depending on any pressure differential on it, and often with a (generally uniform) thickness similar to such films or sheets used in conventional wound dressings, i.e. up to 100 micron, preferably up to 50 micron, more preferably up to 25 micron, and of 10 micron minimum thickness.

The backing layer may often have a rigid and/or resiliently inflexible or stiff area to resist any substantial play between other components that are not mutually integral, and may be stiffened, reinforced or otherwise strengthened, e.g. by a projecting boss.

Such a form of dressing would not be very conformable to the wound bed, and may effectively form a chamber, hollow or cavity defined by a backing layer and the wound bed under the backing layer. It may be desirable that the interior of the wound dressing conform to the wound bed, even for a wound in a highly exuding state. Accordingly, one form of the dressing is provided with a wound filler under the backing layer.

This is favourably a resiliently flexible, e.g. elastomeric, and preferably soft, structure with good conformability to wound shape. It is urged by its own resilience against the backing layer to apply gentle pressure on the wound bed. The wound filler may be integral with the other components of the dressing, in particular the backing layer.

Alternatively, it may be permanently attached to them/it, with an adhesive film, for example, or by heat-sealing, e.g. to a flange or lip extending from the proximal face, so a not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other.

The wound filler may be or comprise a solid integer, favourably a resiliently flexible, e.g. elastomeric, and preferably soft, structure with good conformability to wound shape. Examples of suitable forms of such wound fillers are foams formed of a suitable material, e.g. a resilient thermoplastic.

Preferred materials for the present fillers include reticulated filtration polyurethane foams with small apertures or pores.

Alternatively or additionally, it may be in the form of, or comprise one or more conformable hollow bodies defined by a film, sheet or membrane, such as a bag, chamber, pouch or other structure, filled with a fluid or solid that urges it to the wound shape.

The film, sheet or membrane, often has a (generally uniform) thickness similar to that of films or sheets used in conventional wound dressing backing layers.

That is, up to 100 micron, preferably up to 50 micron, more preferably up to 25 micron, and of 10 micron minimum thickness, and is often resiliently flexible, e.g. elastomeric, and preferably soft.

Such a filler is often integral with the other components of the dressing, in particular the backing layer, or permanently attached to them/it, with an adhesive film, for example, or by heat-sealing, e.g. to a flange Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials.

Examples also include aerosol foams, where the gaseous phase of the aerosol system is air or an inert gas, such as nitrogen or argon, more usually air, at a small positive pressure above atmospheric; and solid particulates, such as plastics crumbs.

Of course, if the backing layer is a sufficiently conformable and/or e.g. an upwardly dished sheet, the backing layer may lie under the wound filler, rather than vice versa.

In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other.

In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer. One form of the dressing is provided with a wound filler under the backing layer that is or comprises a resiliently flexible, e.g. elastomeric, and preferably soft, hollow body defined by a film, sheet or membrane, such as a bag, chamber, pouch or other structure.

It has apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body may then be the aspirating or irrigating fluid in the apparatus.

The hollow body or each of the hollow bodies then effectively forms an inlet pipe or outlet pipe manifold that delivers the aspirating fluid directly to the wound bed or collects the fluid directly from the wound respectively via the holes, openings, orifices, slits or slots, or the tubes, pipes or hoses, etc. in the film, sheet or membrane.

When the therapy is applied in this way, the type of the filler may also be largely determined by the depth and/or capacity of the wound.

Thus, for shallower wounds, examples of suitable wound fillers as a component of a wound dressing include ones that consist essentially of one or more conformable hollow bodies defining an inlet pipe and/or outlet pipe manifold that delivers the aspirating fluid directly to the wound bed or collects the fluid directly from the wound.

A more suitable wound filler for deeper wounds when the therapy is applied in this way may be one which comprises one or more conformable hollow bodies defined by, for example a polymer film, sheet or membrane, that at least partly surround(s) a solid integer. This may provide a system with better rigidity for convenient handling.

The wound filler under the backing layer may effectively form (or be formed by) an inlet pipe or outlet pipe manifold.

If not, in order for aspiration and/or irrigation of the wound bed to occur, it is appropriate for one or more bores, channels, conduits, passages, pipes, tubes, tubules and/or spaces, etc. to run from the point at which the fluid inlet pipe(s) and outlet pipe(s) pass through and/or under the wound-facing face of the backing layer through or around the wound filler under the backing layer.

Less usually, the wound filler may be an open-cell foam with pores that may form such bores, channels, conduits, passages and/or spaces through the wound filler under the backing layer.

Where the filler is or comprises one or more conformable hollow bodies defined by, for example a polymer film, sheet or membrane, it may be provided with means for admitting fluids to the wound bed under the wound dressing.

These may be in the form of pipes, tubes, tubules or nozzles running from the point at which the fluid inlet pipe(s) and outlet pipe(s) pass through and/or under the wound-facing face of the backing layer through or around the wound filler under the backing layer.

All of the suitable layouts for shallower wounds that comprise blind-bore, perforated inlet pipe or outlet pipe manifolds that aspirate fluid in the wound when the dressing is in use, that are described hereinbefore, may be used under a wound filler under the backing layer.

In brief, suitable layouts include ones where one or both manifolds are annular or toroidal (regular, e.g. elliptical or circular or irregular), optionally with blind-bore, perforated radial tubes, pipes or nozzles, branching from the annulus or torus; and/or in a meandering, tortuous, winding, zigzag, serpentine or boustrophedic (i.e. in the manner of a ploughed furrow) pattern, or defined by slots in and apertures through layers attached to each other in a stack.

The inlet and/or outlet tubes, the fluid tube and the fluid supply tube, etc. may be of conventional type, e.g. of elliptical or circular cross-section, and may suitably have a uniform cylindrical bore, channel, conduit or passage throughout their length, and suitably the largest cross-dimension of the bore may be up to 10 mm for large torso wounds, and up to 2 mm for limb wounds.

The tube walls should suitably thick enough to withstand any positive or negative pressure on them. However, the prime purpose of such tubes is to convey fluid irrigant and exudate through the length of the apparatus flow path, rather than to act as pressure vessels. The tube walls may suitably be at least 25 micron thick.

The bore or any perforations, apertures, holes, openings, orifices, slits or slots along the pipes, etc. or in the hollow body or each of the hollow bodies may be of small cross-dimension. They may then effectively form a macroscopic and/or microscopic filter for particulates including cell debris and micro-organisms, whilst allowing proteins and nutrients to pass through.

Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s).

The whole length of the apparatus for aspirating, irrigating and/or cleansing wounds should be microbe-impermeable once the wound dressing is over the wound in use. It is desirable that the wound dressing and the interior of the apparatus for aspirating, irrigating and/or cleansing wounds of the present invention is sterile.

The fluid may be sterilised in the fluid reservoir and/or the rest of the system in which the fluid moves by ultraviolet, gamma or electron beam irradiation.

This way, in particular reduces or eliminates contact of internal surfaces and the fluid with any sterilising agent.

Examples of other methods of sterilisation of the fluid also include e.g. the use of: ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide; although the latter involve contact of internal surfaces and the fluid with the sterilising agent.

It may be desirable that the interior of the wound dressing, the rest of the system in which the fluid moves, and/or the wound bed, even for a wound in a highly exuding state, are kept sterile after the fluid is sterilised in the fluid reservoir, or that at least naturally occurring microbial growth is inhibited.

Thus, materials that are potentially or actually beneficial in this respect may be added to the irrigant initially, and as desired the amount in increased by continuing addition. Examples of such materials include antibacterial agents (some of which are listed above), and antifungal agents. Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate. may be added to adjust the pH, as may local analgesics/anaesthetics, such as lidocaine/lignocaine hydrochloride, xylocaine (adrenaline, lidocaine) and/or anti-inflammatories, to reduce wound pain or inflammation or pain associated with the dressing.

In order to combat the deposition of materials in the flow path from the irrigant, a repellent coating may be used at any point or on any integer in the path in direct contact with the fluid, e.g. on the means for providing aspiration and/or irrigation of the wound or any desired tube or pipe.

Examples of coating materials for surfaces over which the aspirating fluid passes include anticoagulants, such as heparin, and high surface tension materials, such as PTFE, and polyamides, which are useful for growth factors, enzymes and other proteins and derivatives.

The apparatus of the invention for aspirating, irrigating and/or cleansing wounds is provided with means for admitting fluids directly or indirectly to the wound under the wound dressing in the form of a fluid supply tube to a fluid reservoir.

The fluid reservoir for the irrigant may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid. The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body.

In all embodiments of the apparatus the type and material of the tubes throughout the apparatus of the invention for aspirating, irrigating and/or cleansing wounds and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system aspiration and irrigation unit, of the dialysate that moves into the aspirating fluid in the apparatus.

When in contact with irrigant fluid, it should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, e.g. high density polyethylene and polypropylene.

Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

Materials deleterious to wound healing that are removed include oxidants, such as free radicals, e.g. peroxide and superoxide; iron II and iron Ill; all involved in oxidative stress on the wound bed; proteases, such as serine proteases, e.g. elastase and thrombin; cysteine proteases; matrix metalloproteases, e.g. collagenase; and carboxyl (acid) proteases; endotoxins, such as lipopolysaccharides; autoinducer signalling molecules, such as homoserine lactone derivatives, e.g. oxo-alkyl derivatives; inhibitors of angiogenesis such as thrombospondin-1 (TSP-1), plasminogen activator inhibitor, or angiostatin (plasminogen fragment); pro-inflammatory cytokines such as tumour necrosis factor alpha (TNFα) and interleukin 1 beta (IL-1β), oxidants, such as free radicals, e.g. peroxide and superoxide; and metal ions, e.g. iron II and iron Ill, all involved in oxidative stress on the wound bed.

It is believed that aspirating wound fluid aids in removal from of the materials deleterious to wound healing from wound exudate and/or irrigant, whilst distributing materials that are beneficial in promoting wound healing in contact with the wound.

A steady state concentration equilibrium of materials beneficial in promoting wound healing may be set up between in the irrigant and/or wound exudate. Aspirating wound fluid aids in the quicker attainment of this equilibrium.

Materials beneficial to wound healing that are distributed include cytokines, enzymes, growth factors, cell matrix components, biological signalling molecules and other physiologically active components of the exudate and/or materials in the irrigant that are potentially or actually beneficial in respect of wound healing, such as nutrients for wound cells to aid proliferation, gases, such as oxygen.

The conduits through which respectively the irrigant and/or wound exudate passes to and from the wound dressing and i) may have means for modular disconnection and withdrawal of the dressing, ii) providing an immediate fluid-tight seal or closure over the ends of the conduits and the cooperating tubes in the rest of the apparatus of the invention so exposed, to prevent continuing passage of irrigant and/or exudate.

The outlet from the means for aspirate flow regulation and/or tubes may be collected and monitored and used to diagnose the status of the wound and/or its exudate.

Any aspirate collection vessel may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the aspirate collection vessel will be largely determined by its function.

To be suitable for use, the material need only be fluid-impermeable once in use, and flexible.

Examples of suitable materials for the fluid reservoir include synthetic polymeric materials, such as polyolefins, such as poly (vinylidene chloride).

Suitable materials for the present purpose also include polyethylene, e.g. high-density polyethylene, polypropylene, copolymers thereof, for example with vinyl acetate and mixtures thereof.

In a further aspect of the present invention there is provided a conformable wound dressing, characterized in that it comprises: —a backing layer with a wound-facing face which is capable of forming a relatively fluid-tight seal or closure over a wound and has at least one pipe, which passes through and/or under the wound facing face to allow irrigation and/or aspiration of the wound; the point at which at least one pipe passes through and/or under the wound-facing face forming a relatively fluid-tight seal or closure over the wound; and means for applying high frequency vibrational, in particular ultrasonic, energy to the wound bed when in use.

The dressing is advantageously provided for use in a bacteria-proof pouch.

Examples of suitable forms of such wound dressings are as described by way of example hereinbefore.

In a third aspect of the present invention there is provided a method of treating wounds to promote wound healing using the apparatus for aspirating, irrigating and/or cleansing wounds of the present invention.

BRIEF DESCRIPTION OF THE DRAWINGS

The present invention will now be described by way of example only with reference to the accompanying drawings in which, in all schematics, any sonode or sonode-transducer is omitted for clarity.

FIG. 1b is a section view of the apparatus of FIG. 1a.

DETAILED DESCRIPTION

Figure 1A:
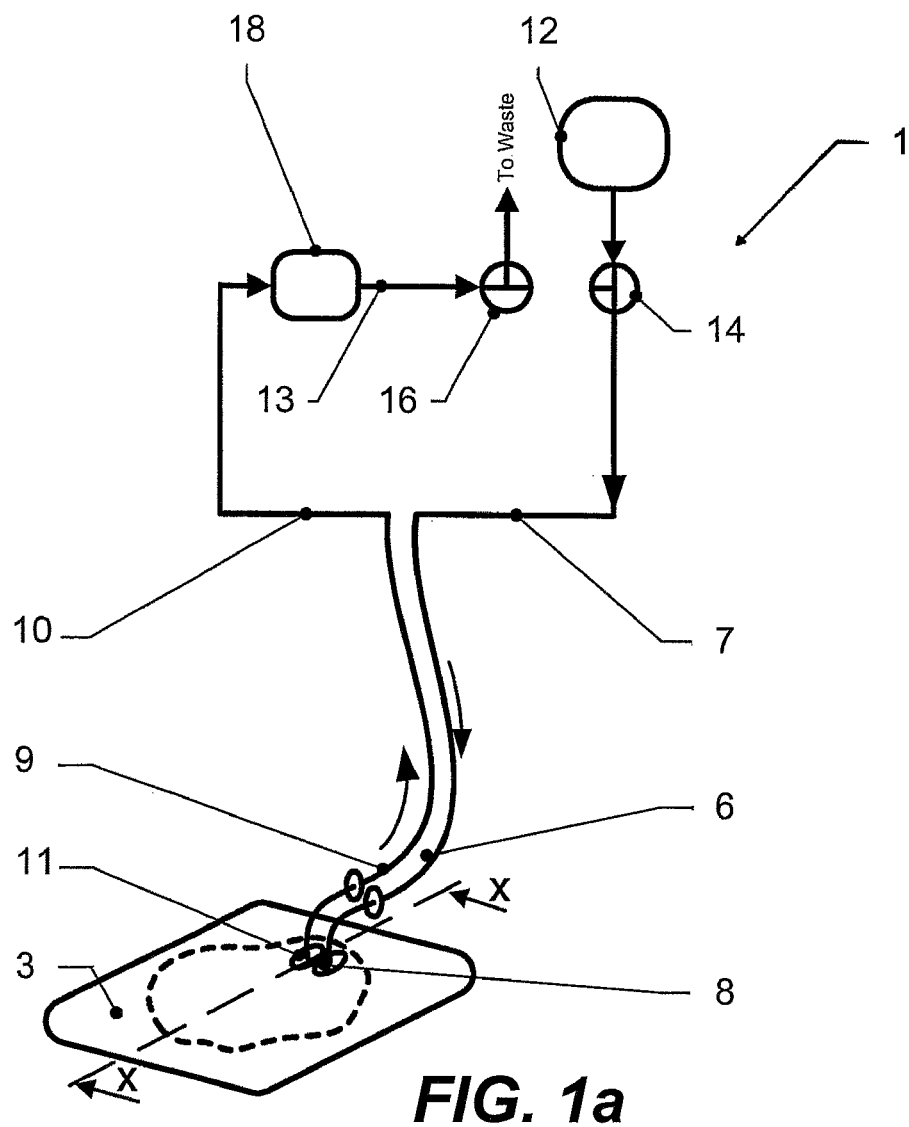
FIG. 1a is a schematic view of an apparatus for aspirating, irrigating and/or cleansing a wound according to the first aspect of the present invention that has a single device for moving fluid through the wound applied to the aspirate in the fluid offtake tube downstream of and away from the wound dressing, in combination with means for supply flow regulation, connected to a fluid supply tube, and means for aspirate flow regulation, connected to a fluid offtake tube.
Figure 1B:
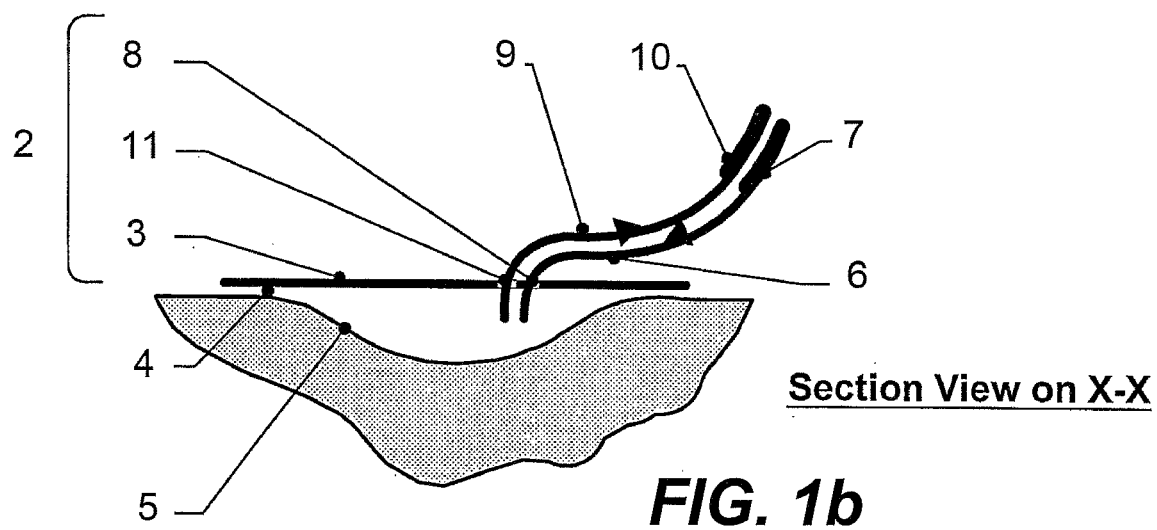

Referring to FIGS. 1a and 1b, the apparatus (1) for aspirating, irrigating and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (5) at (8), and one outlet pipe (9) for connection to a fluid offtake tube (10), which passes through the wound-facing face at (11), the points (8), (11) at which the inlet pipe and the outlet pipe passes through and/or under the wound-facing face forming a relatively fluid-tight seal or closure over the wound; the inlet pipe being connected via means for supply flow regulation, here a valve (14), by the fluid supply tube (7) to a fluid reservoir (12), and the outlet pipe (9) being connected via means for aspirate flow regulation, here a valve (16) and a fluid offtake tube (10) to waste, e.g. to a waste reservoir (19), such as a collection bag; a device for moving fluid through the wound (17), here a diaphragm pump (18), e.g. preferably a small portable diaphragm pump, acting on the fluid aspiration tube (13) to apply a low negative pressure on the wound; and the valve (14) in the fluid supply tube (7), the valve (16) in the fluid offtake tube (10), and the diaphragm pump (18), providing means for providing simultaneous aspiration and irrigation of the wound (17), such that fluid may be supplied to fill the flow path from the fluid reservoir via the fluid supply tube (via the means for supply flow regulation) and moved by the device through the flow path.

The operation of the apparatus is as described herein before.

Figure 2:
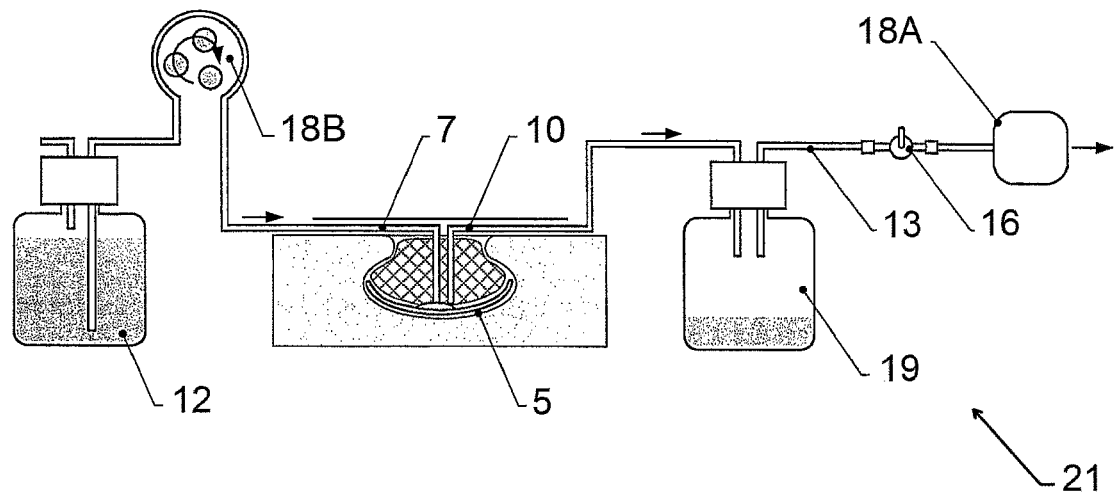
FIG. 2 is a schematic view of another apparatus for aspirating, irrigating and/or cleansing a wound according to the first aspect of the present invention that has a first device for moving fluid through the wound applied to the aspirate in the fluid offtake tube downstream of and away from the wound dressing, with means for aspirate flow regulation, connected to a fluid offtake tube; and a second device for moving fluid through the wound applied to the irrigant in the fluid supply tube upstream of and towards the wound dressing.

Referring to FIG. 2, the apparatus (21) is a variant two-pump system with essentially identical, and identically numbered, components as in FIG. 1, except that there is no means for supply flow regulation in the fluid supply tube (7) from the fluid reservoir (128), and there is a first device for moving fluid through the wound (17), here a diaphragm pump (18A), e.g. preferably a small portable diaphragm pump, acting on the fluid aspiration tube (13) downstream of and away from the wound dressing to apply a low negative pressure on the wound; with means for aspirate flow regulation here a valve (16) connected to the fluid offtake tube (10) and a vacuum vessel (aspirate collection jar) (12A); and a second device for moving fluid through the wound (17), here a peristaltic pump (188), e.g. preferably a small portable diaphragm pump, applied to the irrigant in the fluid supply tube (7) upstream of and towards the wound dressing, the first device (18A) and second device (188), and the valve (16) in the fluid offtake tube (10), and the diaphragm pump (18), providing means for providing simultaneous aspiration and irrigation of the wound (17), such that fluid may be supplied to fill the flow path from the fluid reservoir via the fluid supply tube (via the means for supply flow regulation) and moved by the devices through the flow path.

The operation of the apparatus is as described hereinbefore

Figure 3:
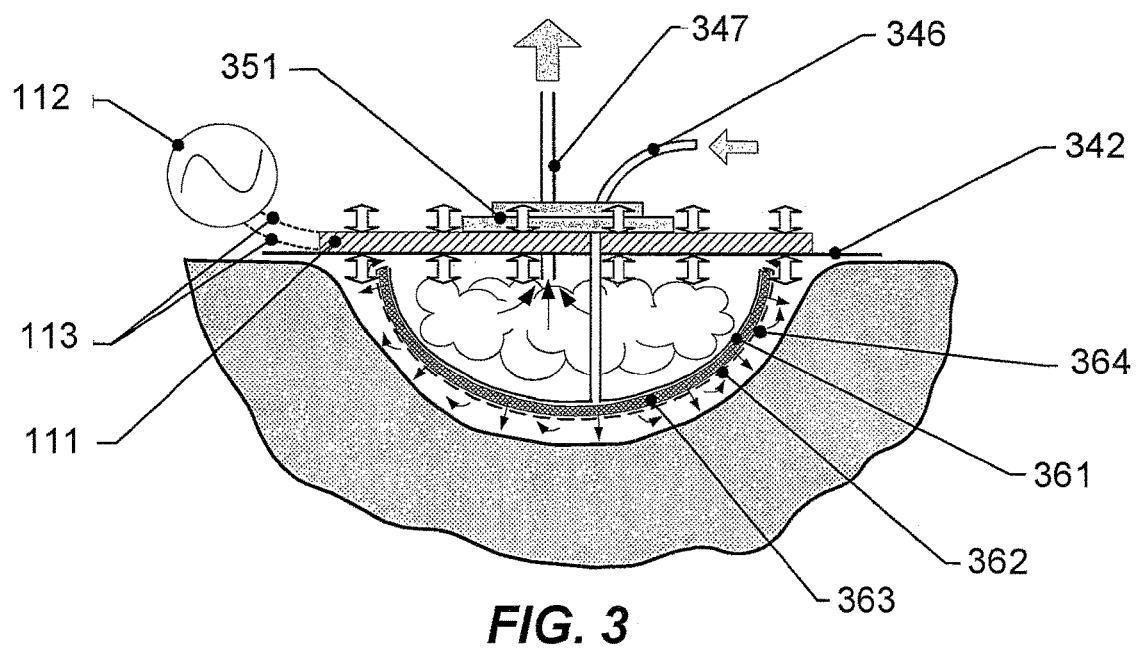
FIGS. 3 to 7 are cross-sectional views of conformable wound dressings, of the second aspect of the present invention for aspirating and/or irrigating wounds.

Referring to FIG. 3, a form of dressings for deeper wounds is shown. This comprises a circular backing layer (342) and a chamber (363) in the form of a deeply indented disc much like a multiple Maltese cross.

This is defined by an upper impervious membrane (361) and a lower porous film (362) with apertures (364) that deliver the irrigant fluid directly from the wound bed over an extended area.

The chamber (363) is able to conform well to the wound bed by the arms closing in and possibly overlapping in insertion into the wound. The space above the chamber (363) is filled with an elastically resilient foam or loose gauze.

A piezoelectric sonode-transducer (111) is mounted on the upper face of the backing layer (342), and is connected to an ultrasonic frequency electrical signal generator run at the appropriate frequencies (112) (shown schematically) by electrical leads (113).

It is a sheet or membrane of a piezoelectric transducing polyolefin, such as polyvinylidene fluoride and copolymers thereof, and is adhered with a curable adhesive to the dressing.

An inlet pipe (346) and outlet pipe (347) are mounted centrally in a boss (351) on the sonode-transducer (111) on the backing layer (342), and pass through both.

The inlet pipe (346) communicates with the interior of the chamber (348). The outlet pipe (347) extends radially to just below the backing layer (342) to communicate with the interior of the pouch (363).

Figure 4:
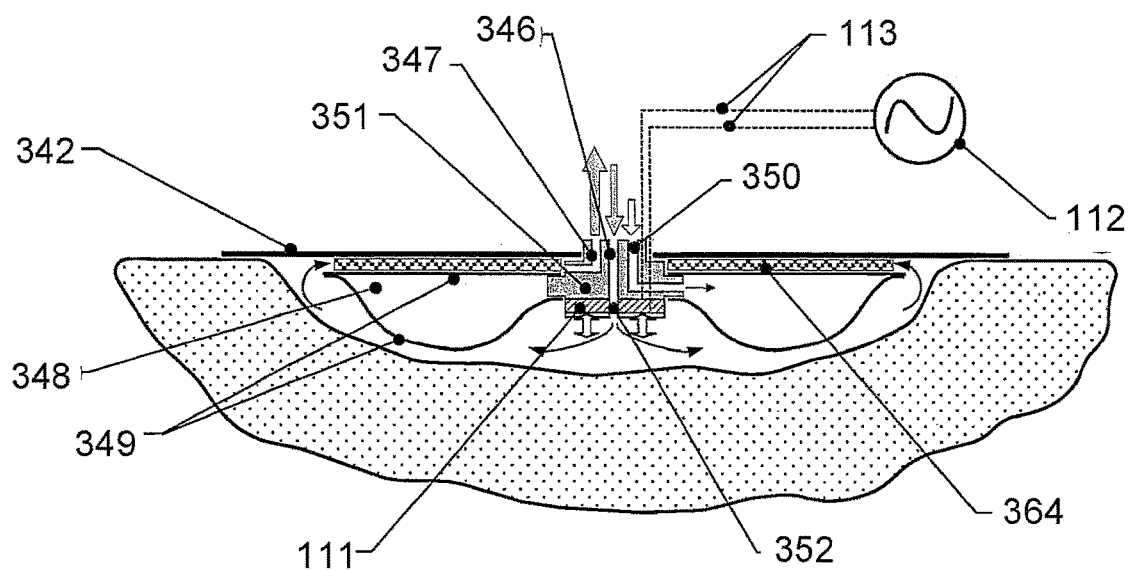

Referring to FIG. 4, this form of the dressing is provided with a wound filler (348) under a circular backing layer (342).

The filler (348) comprises a generally downwardly domed toroidal conformable hollow body, defined by a membrane (349) which is filled with a fluid, here air or nitrogen that urges it to the wound shape. The filler (348) is permanently attached to the backing layer via a boss (351), which is e.g. heat-sealed to the backing layer (342).

An annular layer of foam (364) formed of a suitable material, e.g. a resilient thermoplastic, surrounds the boss (351). Preferred foam materials include reticulated filtration polyurethane foams with small apertures or pores.

A piezoelectric sonode-transducer (111) is mounted on the underside of the boss (351), and is connected to an ultrasonic frequency electrical signal generator run at the appropriate frequencies (112) (shown schematically) by electrical leads (113) running through the boss (351).

It is a sheet or membrane of a piezoelectric transducing polyolefin, such as polyvinylidene fluoride and copolymers thereof, and is adhered by heat lamination to the dressing.

An inflation inlet pipe (350), inlet pipe (346) and outlet pipe (347) are mounted centrally in the boss (351) in the backing layer (342). The inflation inlet pipe (350) communicates with the interior of the hollow body (348), to permit inflation of the body (348). The inlet pipe (346) extends in a pipe (352) through boss (351).

The outlet pipe (347) extends radially immediately under the backing layer (342), and collects fluid flowing radially through the foam layer (364) from the wound periphery when the dressing is in use.

Figure 5:
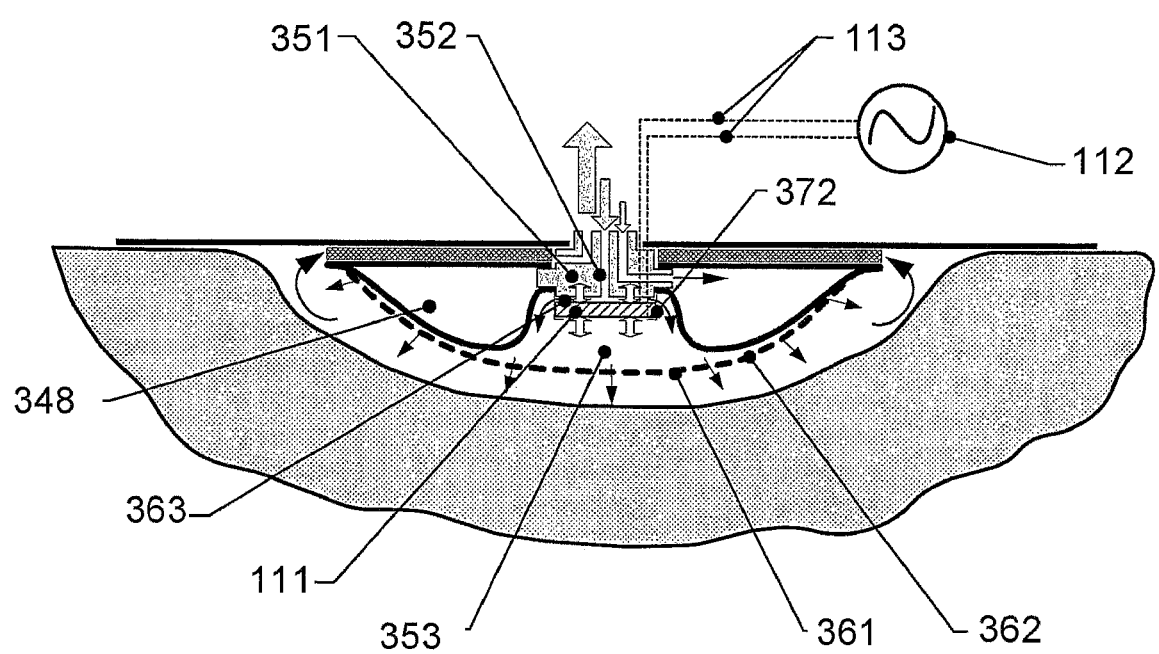

Referring to FIG. 5, this form of the dressing is a variant of that of FIG. 4, with identical, and identically numbered, components, except for the following:

A downwardly domed membrane (361) with apertures (362) is permanently attached at its periphery by heat-sealing to, and lies underneath, the filler (348), to form an inlet manifold (353). The pipe (352) communicates with the interior of the inlet manifold (353), but not through the piezoelectric sonode-transducer (111).

Figure 6:
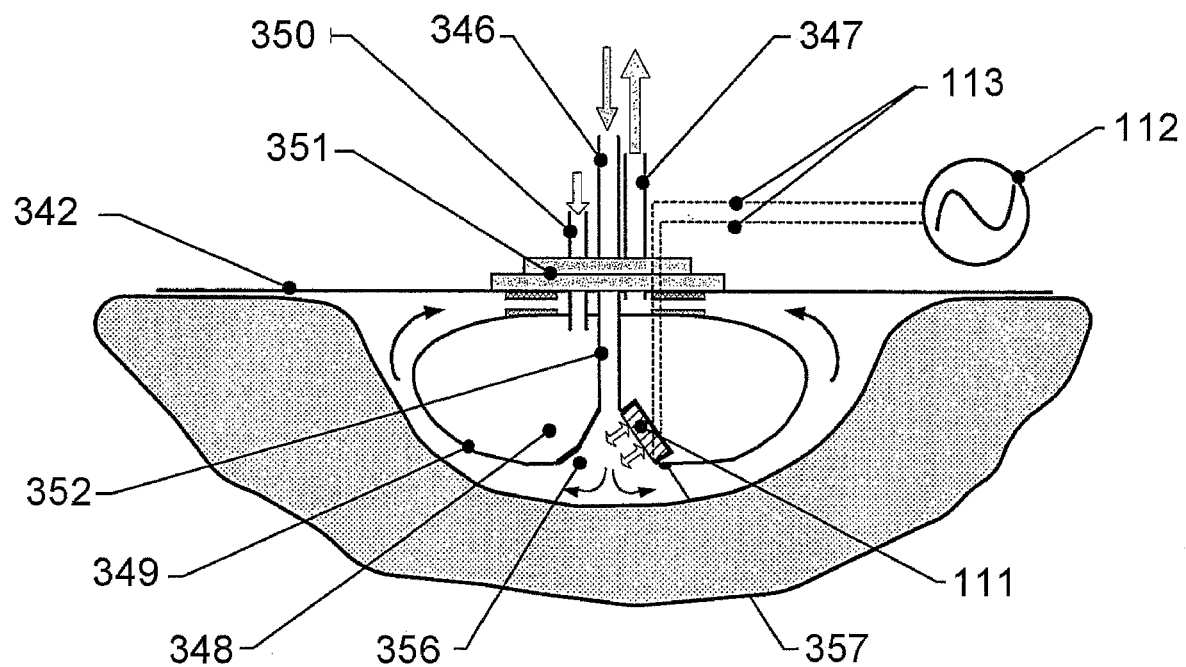

This is still mounted on the underside of the boss (351), but spaced from it by struts (372) defining peripheral channels or conduits (363) that communicate between the pipe (352) and the inlet manifold (353). Referring to FIG. 6, the dressing is also provided with a wound filler (348) under a circular backing layer (342). This comprises a generally oblately spheroidal conformable hollow body, defined by a membrane (349) which is filled with a fluid, here air or nitrogen, that urges it to the wound shape. The filler (348) is permanently attached to the backing layer via a boss (351), which is e.g. heat-sealed to the backing layer (342).

An inflation inlet pipe (350), inlet pipe (346) and outlet pipe (347) are mounted centrally in the boss (351) in the backing layer (342) above the hollow body (348). The inflation inlet pipe (350) communicates with the interior bf the hollow body (348), to permit inflation of the body (348). The inlet pipe (346) extends in a pipe (352) effectively through the hollow body (348). The outlet pipe (347) extends radially immediately under the backing layer (342).

The lower end of the inlet pipe (346) is splayed into a funnel (356), in part of the wall of which is a recess (357). A sonode-transducer, such as an Exogen™ device (111) is a tight push fit in the recess.

It is connected to an ultrasonic frequency electrical signal generator run at the appropriate frequencies (112) (shown schematically) by electrical leads (113) running through the boss (351) and the hollow body (348).

Figure 7:
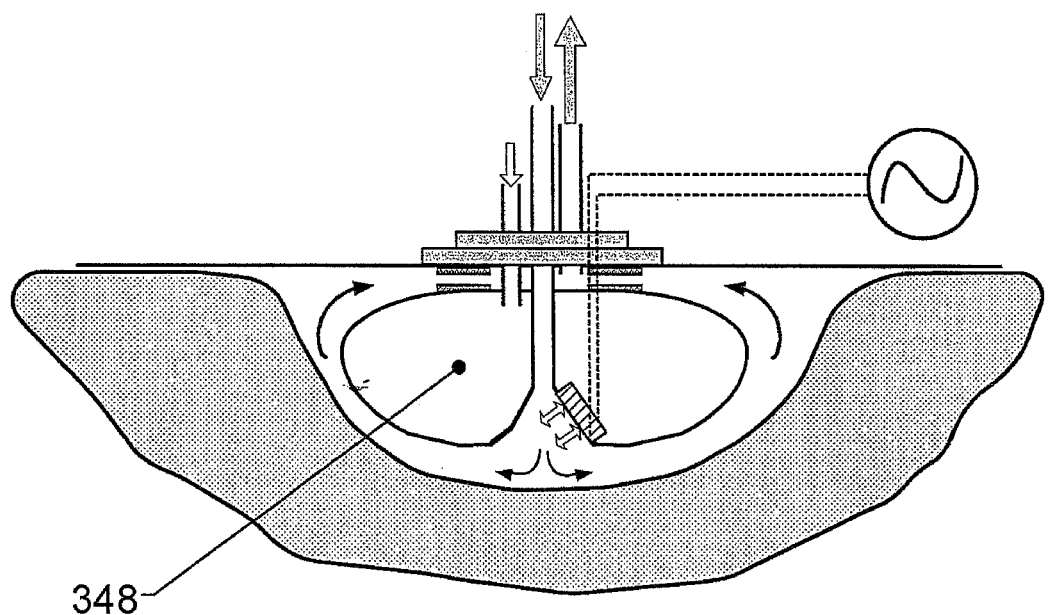

Referring to FIG. 7, this form of the dressing is a variant of that of FIG. 6, with identical, and identically numbered, components, except that the sonode-transducer, whilst mounted in the same overall position is not in a recess, but within the hollow body (348).

This form of the dressing is a more suitable layout for deeper wounds.

Figure 8A:
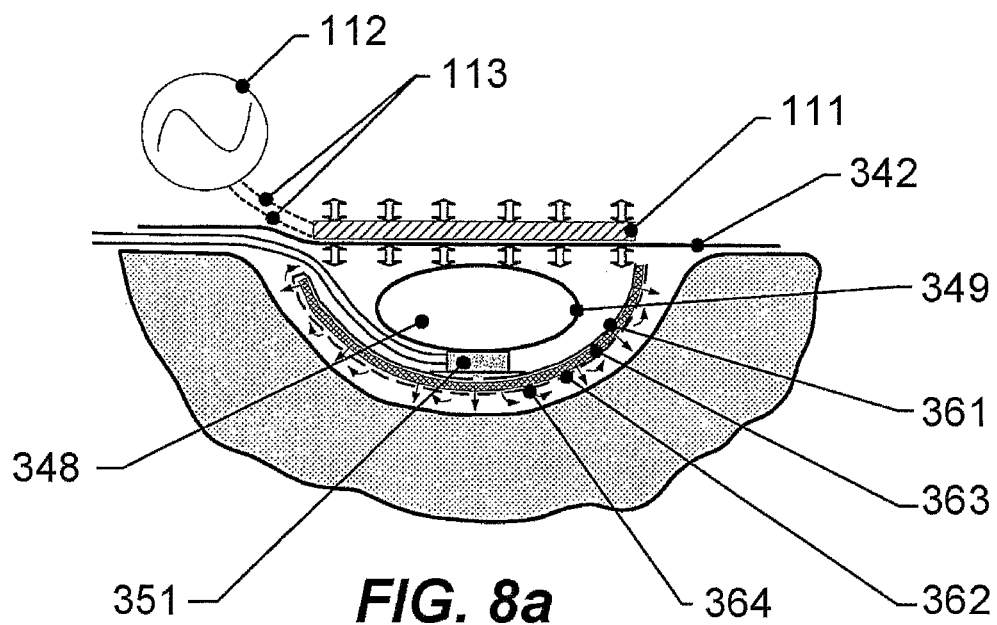
FIGS. 8A to 8C show another example embodiment of a conformable wound dressing, of the second aspect of the present invention for aspirating and/or irrigating wounds.

Referring to FIG. 8a, another form for deeper wounds is shown.

This comprises a circular, or more usually square or rectangular backing layer (342) and a chamber (363) in the form of a deeply indented disc much like a multiple Maltese cross or a stylized rose.

Figure 8B:
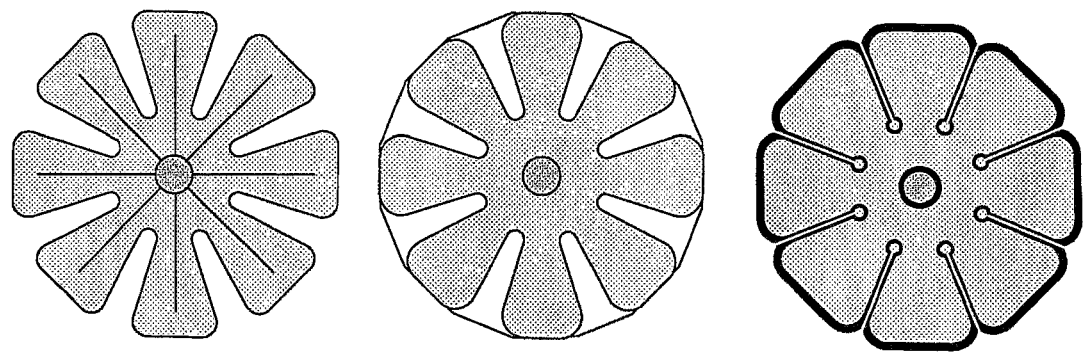
Figure 8C:
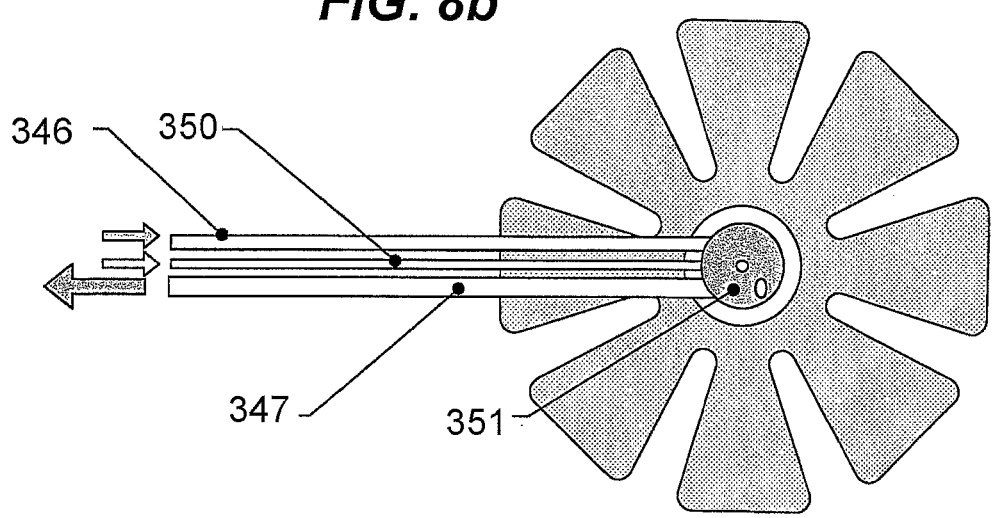

This is defined by an upper impervious membrane (361) and a lower porous film (362) with apertures (364) that deliver the irrigant fluid directly to the wound bed over an extended area, and thus effectively forms an inlet manifold. Three configurations of the chamber (363) are shown in FIG. 8b, all of which are able to conform well to the wound bed by the arms closing in and possibly overlapping in insertion into the wound.

The space above the chamber (363) is filled with a wound filler (348) under the backing layer (342). This comprises an oblately spheroidal conformable hollow body, defined by a membrane (349) that is filled with a fluid, here air or nitrogen, that urges it to the wound shape.

A piezoelectric sonode-transducer (111) is mounted on the upper face of the backing layer (342), and is connected to an ultrasonic frequency electrical signal generator run at the appropriate frequencies (112) (shown schematically) by electrical leads (113).

It is a sheet or membrane of a piezoelectric transducing polyolefin, such as polyvinylidene fluoride and copolymers thereof, and is adhered with a curable adhesive to the dressing.

A moulded hat-shaped boss (351) is mounted centrally on the upper impervious membrane (361) of the chamber (363). It has three internal channels, conduits or passages through it (not shown), each with entry and exit apertures. The filler (348) is attached to the membrane (361) of the chamber (363) by adhesive, heat welding or a mechanical fixator, such as a cooperating pin and socket.

An inflation inlet pipe (350), inlet pipe (346) and outlet pipe (347) pass under the edge of the proximal face of the backing layer (342) of the dressing, and extend radially immediately under the filler (348) and over the membrane (361) of the chamber (363) to each mate with an entry aperture in the boss (351).

An exit to the internal channel, conduit or passage through it that receives the inflation inlet pipe (350) communicates with the interior of the hollow filler (348), to permit inflation.

An exit to the internal channel, conduit or passage that receives the inlet pipe (346) communicates with the interior of the chamber (363) to deliver the irrigant fluid via the chamber (363) to the wound bed over an extended area.

Similarly, an exit to the internal channel, conduit or passage that receives the outlet pipe (347) communicates with the space above the chamber (363) and under the wound filler (348), and collects flow of irrigant and/or wound exudate radially from the wound periphery.

Figure 9A:
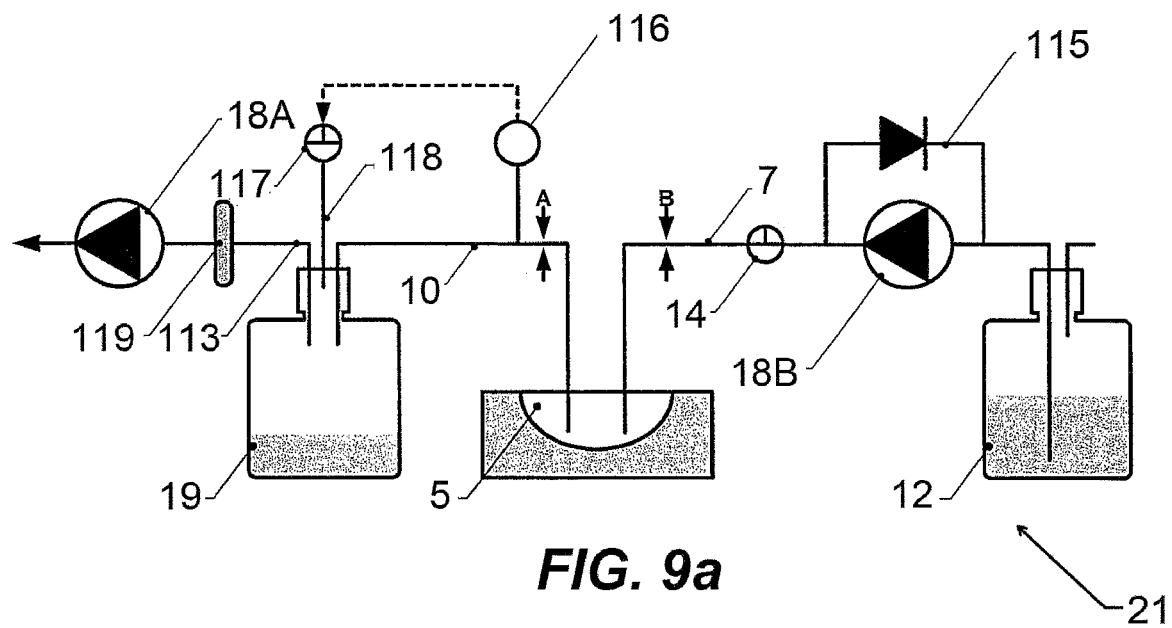
FIGS. 9A to D are variants of a two-pump system with essentially identical, and identically numbered, components as in FIG. 2, except that there is a pump bypass loop, a filter downstream of the aspirate collection vessel, and a bleed regulator, such as a rotary valve, connected to the fluid offtake tube or to the wound space, for the regulation of the positive or negative pressure applied to the wound.

Referring to FIG. 9A, the apparatus (21) is a variant two-pump system with essentially identical, and identically numbered, components as in FIG. 2.

Thus, there is a means for supply flow regulation, here a valve (14) in the fluid supply tube (7) from the fluid reservoir (128), and a first device for moving fluid through the wound (17), here a fixed-speed diaphragm pump (18A), e.g. preferably a small portable diaphragm pump, acting not on the fluid aspiration tube (13), but on an air aspiration tube (113) downstream of and away from an aspirate collection vessel (12A) to apply a low negative pressure on the wound through the aspirate collection vessel (12A); with a second device for moving fluid through the wound (17), here a fixed speed peristaltic pump (188), e.g. preferably a small portable peristaltic pump, applied to the irrigant in the fluid supply tube (7) upstream of and towards the wound dressing, the first device (18A) and second device (188), and the valve (14) in the fluid supply tube (7), providing means for providing simultaneous aspiration and irrigation of the wound (17), such that fluid may be supplied to fill the flow path from the fluid reservoir via the fluid supply tube (via the means for supply flow regulation) and moved by the devices through the flow path.

There is no means for aspirate flow regulation; e.g. a valve connected to the fluid offtake tube (10).

Since first device (18A) and second device (188) are fixed-speed, the valve (14) in the fluid supply tube (7) provides the sole means for varying the irrigant flow rate and the low negative pressure on the wound.

The following extra features are present:

The second device, the fixed-speed peristaltic pump (18B), is provided with means for avoiding over-pressure, in the form of a bypass loop with a nonreturn valve (115). The loop runs from the fluid supply tube (7) downstream of the pump (18B) to a point in the fluid supply tube (7) upstream of the pump (18B).

A pressure monitor (116) connected to the fluid offtake tube (10) has a feedback connection to a bleed regulator, here a motorised rotary valve (117) on a bleed tube (118) running to and centrally penetrating the top of the aspirate collection vessel (12A). This provides means for holding the low negative pressure on the wound at a steady level.

A filter (119) downstream of the aspirate collection vessel (12A) prevents passage of gas- (often air-) borne particulates, including liquids and micro-organisms, from the irrigant and/or exudate that passes into the aspirate collection vessel (12A) into the first device (18A). At the same time, it allows the carrier gas to pass through the air aspiration tube (113) downstream of it to the first device (18A).

The operation of the apparatus is as described hereinbefore

Figure 9B:
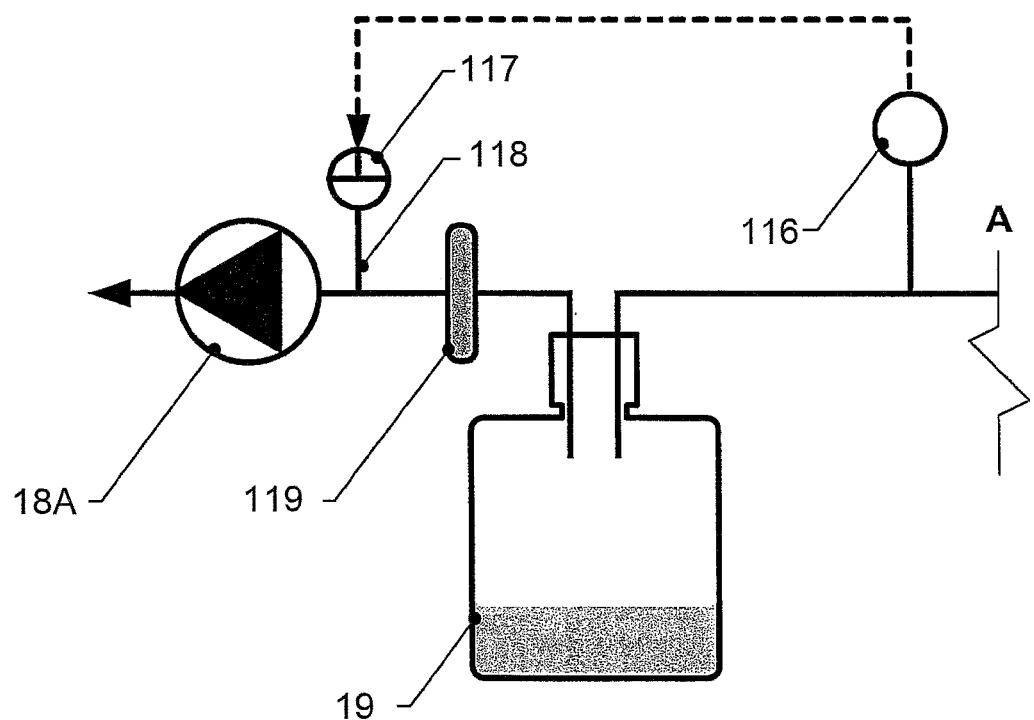

Referring to FIG. 9B, this shows an alternative layout of the essentially identical, and identically numbered, components in FIG. 9A downstream of point A in FIG. 9A. The bleed tube (118) runs to the air aspiration tube (113) downstream of the filter (119), rather than into the aspirate collection vessel (12A). This provides means for holding the low negative pressure on the wound at a steady level. The operation of the apparatus is as described hereinbefore.

Figure 9C:
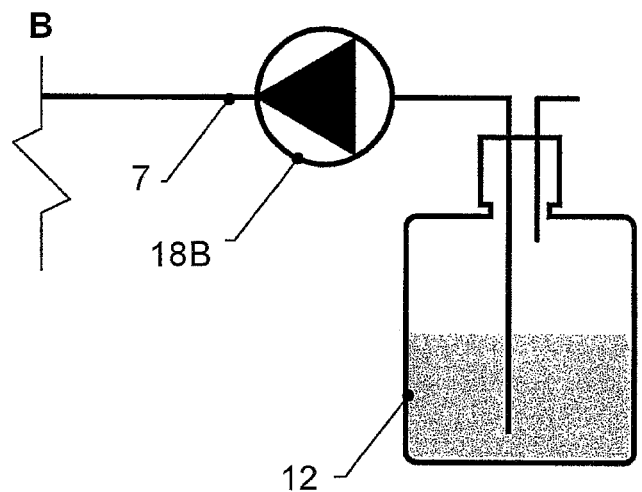
Figure 9D:
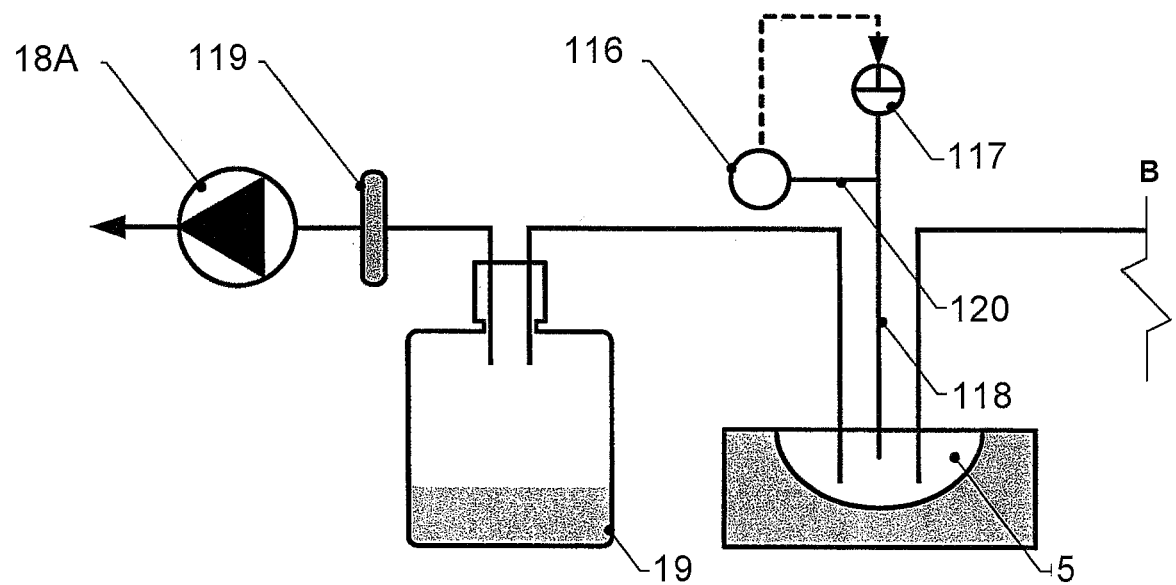

Referring to FIG. 9C, this shows an alternative layout of the essentially identical, and identically numbered, components in FIG. 9A upstream of point B in FIG. 9A. The second device (188) is a variable-speed pump, and the valve (14) in the fluid supply tube (7) is omitted. The second device (188) is the sole means for varying the irrigant flow rate and the low negative pressure on the wound. The operation of the apparatus is as described hereinbefore Referring to FIG. 9O, this shows an alternative layout of the essentially identical, and identically numbered, components in FIG. 9A downstream of point 8 in FIG. 9A.

The pressure monitor (116) is connected to a monitor offtake tube (120) and has a feedback connection to the bleed regulator, motorised rotary valve (117) on a bleed tube (118) running to the monitor offtake tube (120). This provides means for holding the low negative pressure on the wound at a steady level. The operation of the apparatus is as described hereinbefore.

Figure 10A:
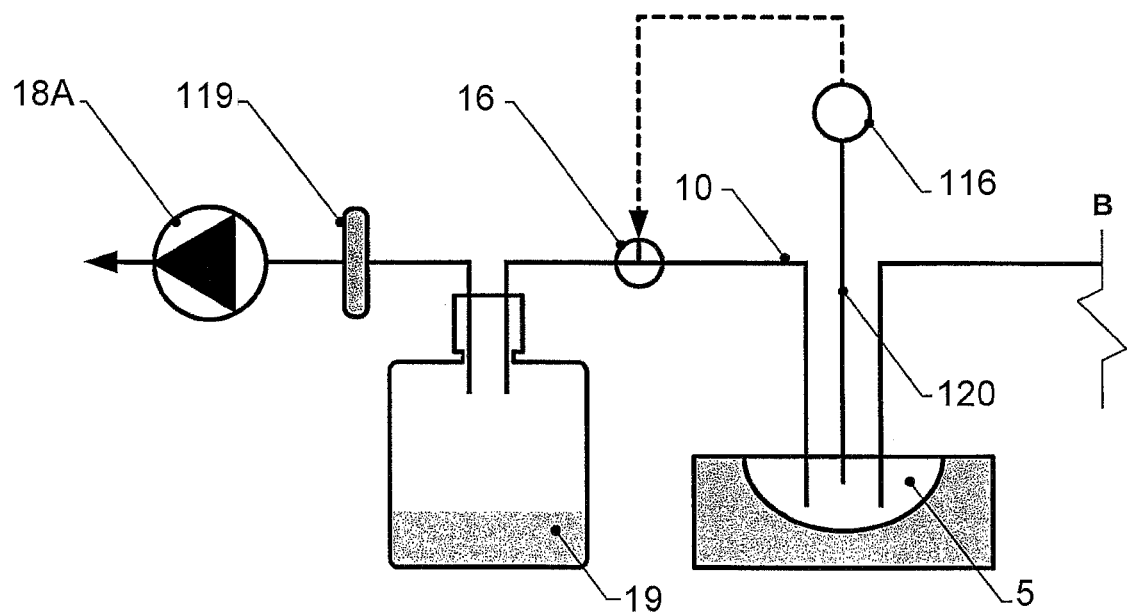
FIGS. 10A to C are variants of a two-pump system with essentially identical, and identically numbered, components as in FIG. 11, except that they have various means for varying the regulation of the positive or negative pressure applied to the wound.

Referring to FIG. 10A, this shows another alternative layout of the essentially identical, and identically numbered, components in FIG. 9A downstream of point 8 in FIG. 9A.

The pressure monitor (116) is connected to a monitor offtake tube (120) and has a feedback connection to a means for aspirate flow regulation, here a motorised valve (16) in the air aspiration tube (113) downstream of the filter (119).

Figure 10B:
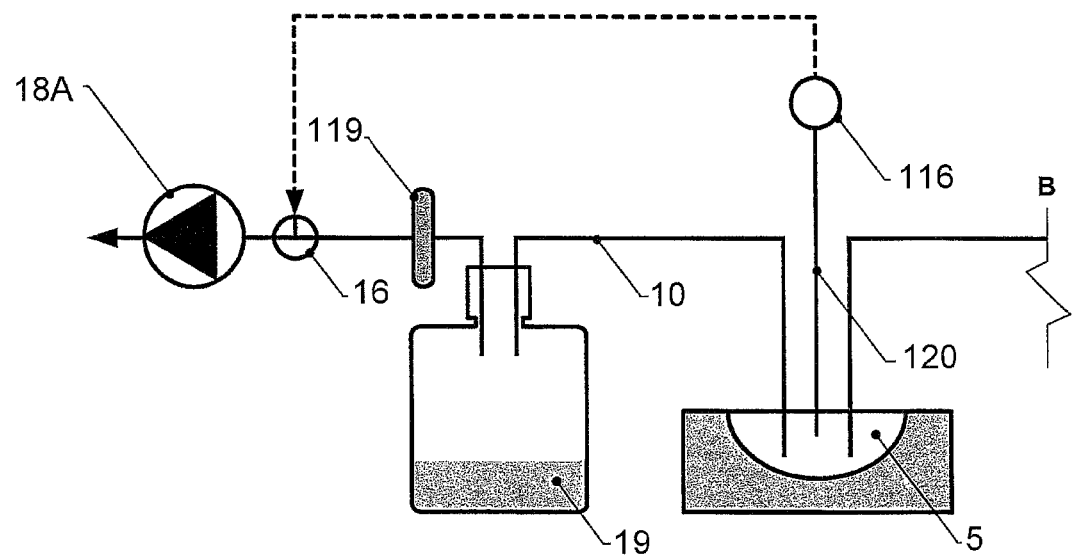

This provides means for aspirate flow regulation and for holding the low negative pressure on the wound at a steady level. The operation of the apparatus is as described hereinbefore Referring to FIG. 10B, this shows another alternative layout of the essentially identical, and identically numbered, components in FIG. 10A downstream of point B in FIG. 9A. The pressure monitor (116) is connected to a monitor offtake tube (120) and has a feedback connection to a means for aspirate flow regulation, here a motorised valve (16), in the fluid offtake tube (10) upstream of the aspirate collection vessel (12A).

This provides means for aspirate flow regulation and for holding the low negative pressure on the wound at a steady level. The operation of the apparatus is as described hereinbefore Referring to FIG. 10C, this shows another alternative layout of the essentially identical, and identically numbered, components in FIG. 10A downstream of point B in FIG. 9A. The pressure monitor (116) is connected to a monitor offtake tube (120) and has a feedback connection to a variable-speed first device (1 SA), here a variable-speed pump, downstream of the filter (119), and the valve (16) in the fluid offtake tube (10) is omitted.

This provides means for aspirate flow regulation and for holding the low negative pressure on the wound at a steady level. The operation of the apparatus is as described hereinbefore.

Figure 10C:
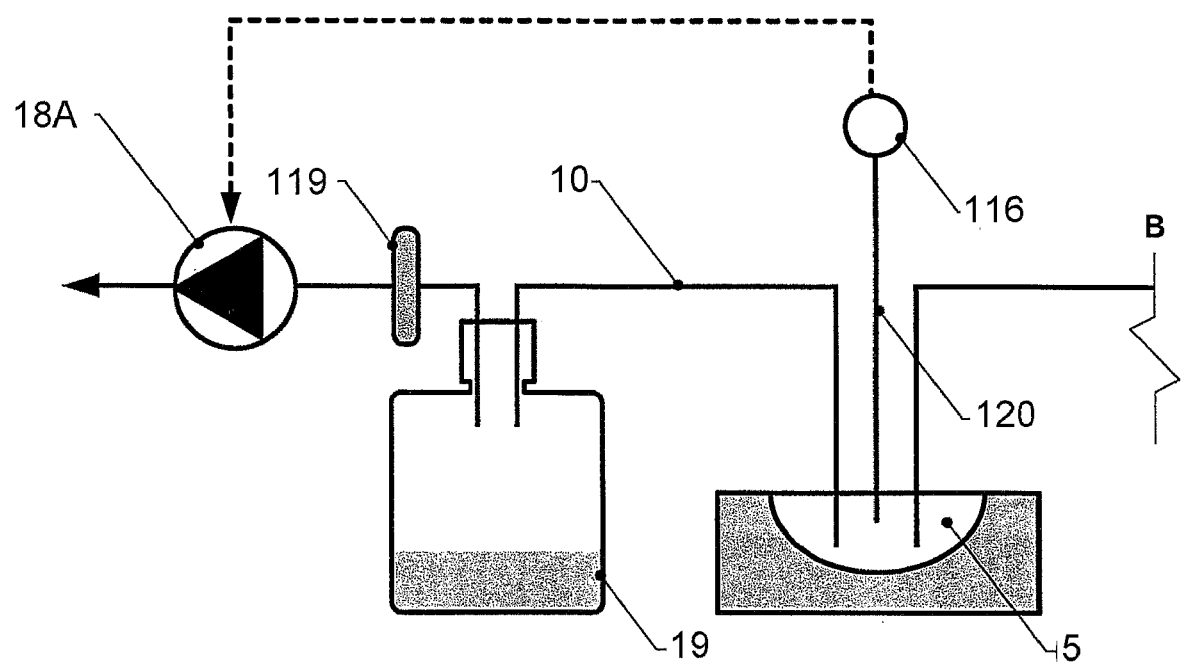
Figure 11A:
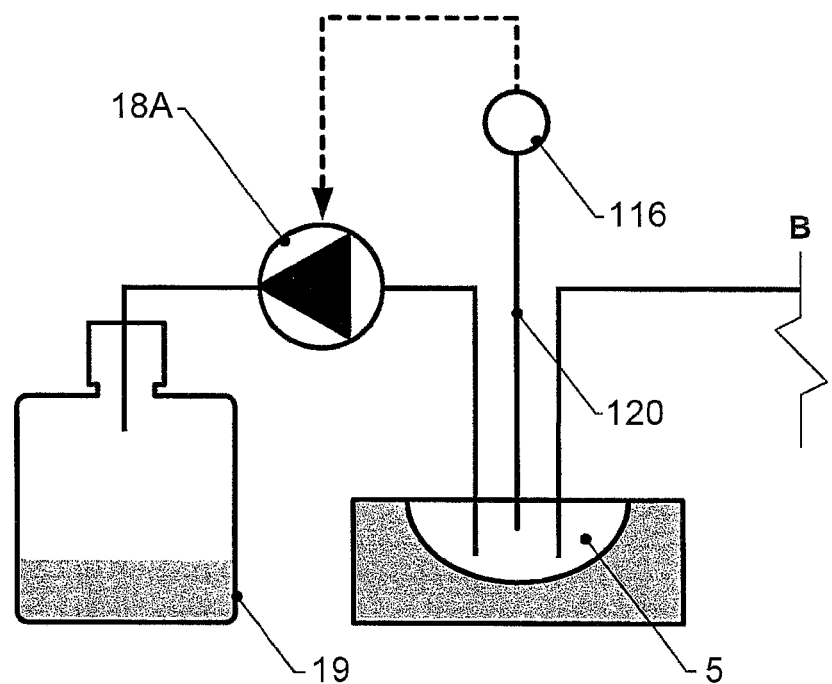
FIGS. 11A and B are variants of a two-pump system with essentially identical, and identically numbered, components as in FIGS. 9A to 9O. However, they have alternative means for handling the aspirate flow to the aspirate collection vessel under negative or positive pressure to the wound in simultaneous aspiration and irrigation of the wound, including in FIG. 11B a third device for moving fluid into a waste bag.

Referring to FIG. 11A, this shows another alternative layout of the essentially identical, and identically numbered, components in FIG. 10C downstream of point B in FIG. 9A, and alternative means for handling the aspirate flow to the aspirate collection vessel under negative or positive pressure to the wound. The pressure monitor (116) is connected to a monitor offtake tube (120) and has a feedback connection to a variable speed first device (18A), here a variable-speed pump, upstream of the aspirate collection vessel (12A), and the filter (119) and the air aspiration tube (113) are omitted. This provides means for aspirate flow regulation and for holding the low negative pressure on the wound at a steady level. The operation of the apparatus is as described hereinbefore.

Figure 11B:
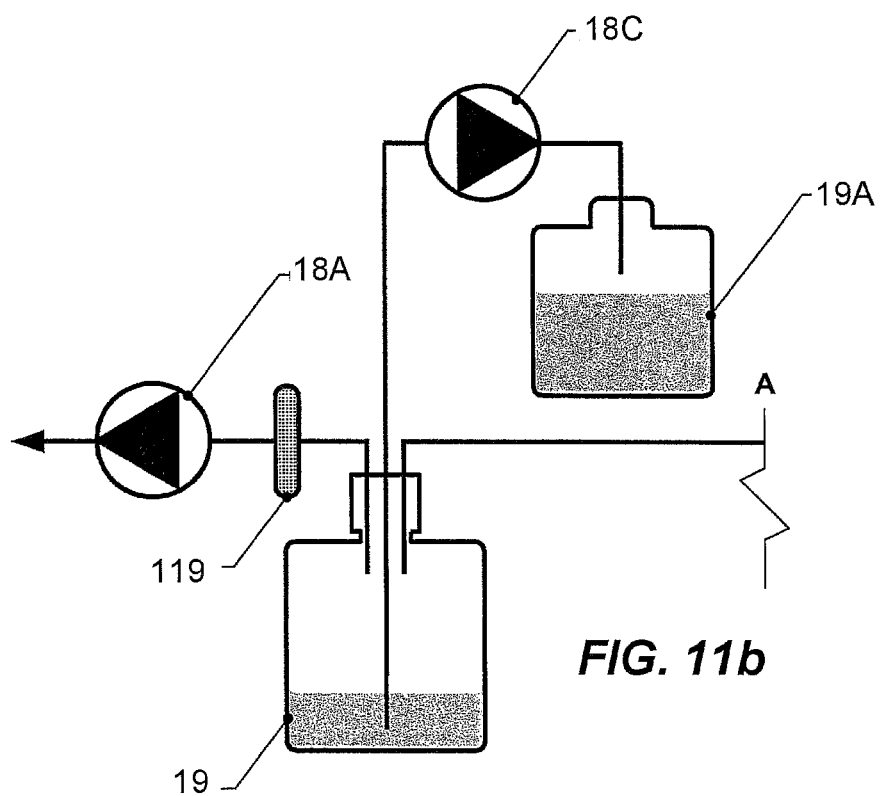

Referring to FIG. 11B, this shows another alternative layout of the essentially identical, and identically numbered, components in FIG. 10C downstream of point B in FIG. 9A, and alternative means for handling the aspirate flow to the aspirate collection vessel under negative or positive pressure to the wound. The pressure monitor (116) is omitted, as is the feedback connection to a variable-speed first device (18A), here a variable speed pump, downstream of the aspirate collection vessel (12A) and the filter (119).

A third device (18C), here a fixed-speed pump, provides means for moving fluid from the aspirate collection vessel (12A) into a waste bag (12C). The operation of the apparatus is as described herein before.

Figure 12:
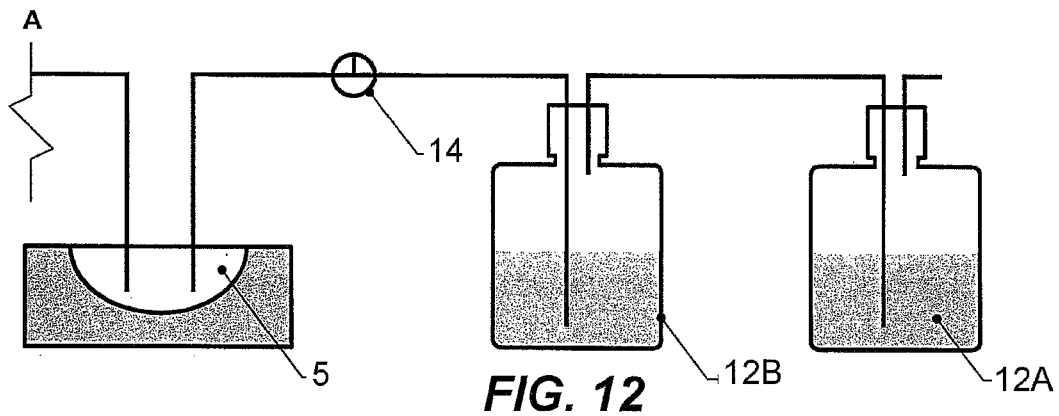
FIG. 12 is a single-pump system essentially with the omission from the apparatus of FIG. 11 of the second device for moving irrigant fluid into the wound dressing.

Referring to FIG. 12, this shows an alternative layout of the essentially identical, and identically numbered, components in FIG. 9A upstream of point A in FIG. 9A.

It is a single-pump system essentially with the omission from the apparatus of FIG. 9A of the second device for moving irrigant fluid into the wound dressing. The operation of the apparatus is as described hereinbefore.

Figure 13:
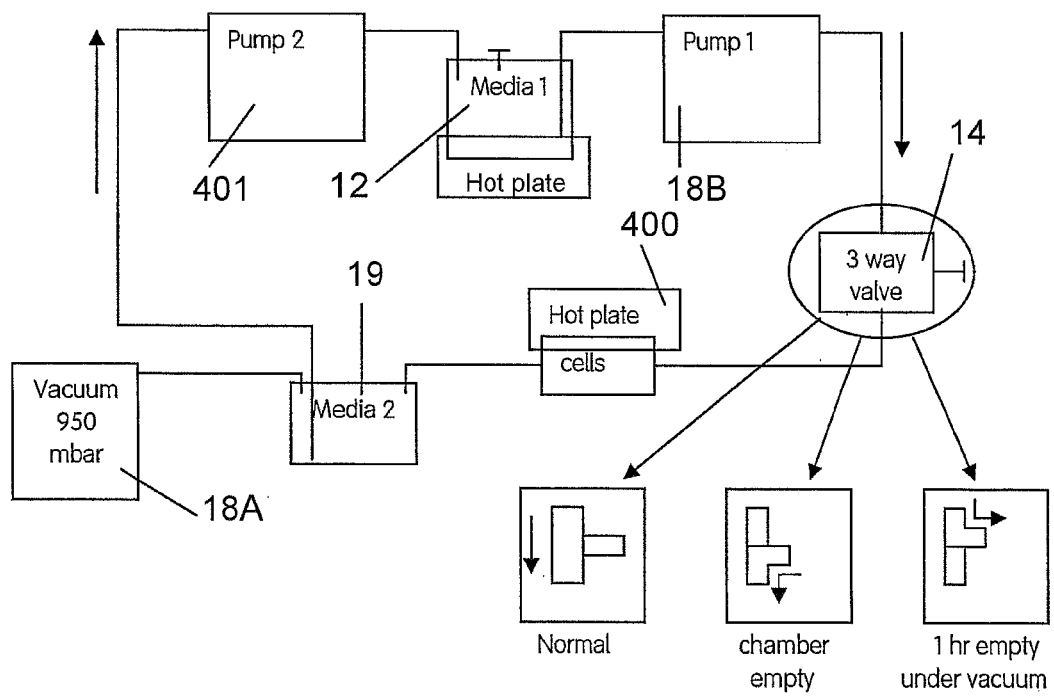
FIG. 13 shows a suitable apparatus for in vitro assessment of the effects of ultrasound on cells in a simulated wound.
Figure 14:
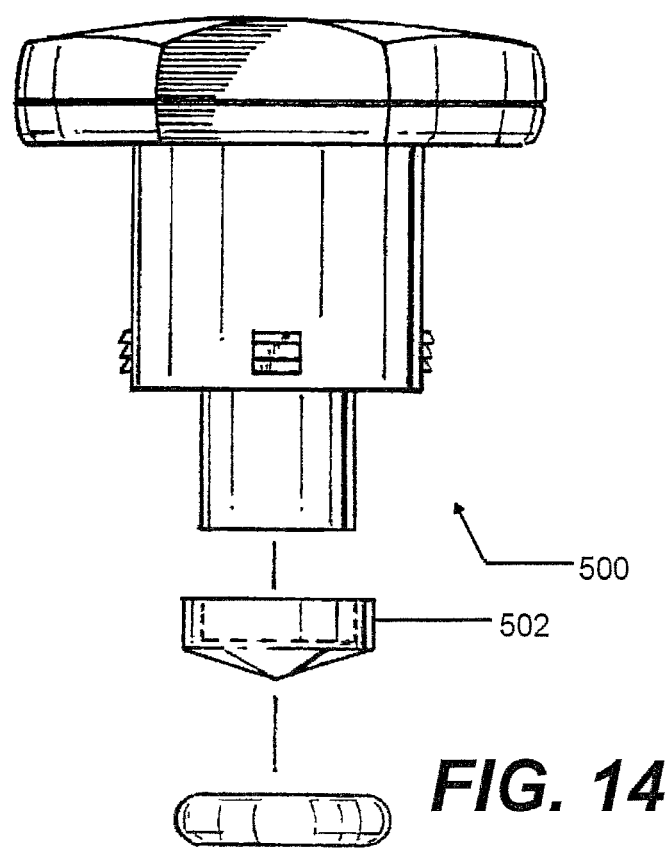
FIG. 14 shows an example format for a transducer including a focusing element for focusing the propagation of ultrasound at a predetermined angle.

Referring to FIG. 13, a suitable apparatus for assessing the effects of ultrasound treatment on cells in a simulated wound is shown.

Pump (188) pumps irrigation fluid from an irrigant reservoir (12) through a 3-way valve (14), which can be configured to allow continuous flow through the test chamber (400), emptying of the test chamber (400) under vacuum, or emptying of the test chamber (400) at atmospheric pressure.

The irrigant passes into the test chamber (400), which is described in more detail later. The aspirate leaving the test chamber (400) passes into a waste reservoir (19). A source of vacuum (18A) is used to maintain the system at a vacuum (950 mbar), and draws the aspirate from the test chamber (400) into the waste reservoir (19). This source of vacuum (18A) is typically a vacuum pump. An additional pump (401) recycles the aspirate from the waste reservoir (19) to the irrigant reservoir (12). This system is useful in a test apparatus, but would generally not be suitable when treating a patient as the aspirate would typically be contaminated and should be disposed of.

An apparatus of the present invention was constructed essentially as in FIG. 13. The circuit shown in FIG. 13 can be used for either sequential or simultaneous irrigation/aspiration.

The circuit has the means for fluid cleansing of a wound using an apparatus where an irrigant or fluid of some nature is delivered continually to the (simulated) wound bed and the resultant wound exudate/fluid mixture is at the same time continually aspirated from the wound and is pumped to waste. (For the experiments the aspirant was not pumped to waste but was re-circulated.) The circuit was also used to provide a system where the wound is subjected to repeated iteration of a cycle of fluid delivery followed by a period of aspiration under reduced pressure.

The apparatus comprises a surrogate wound chamber (400) (Minucells perfusion chamber) in which normal diploid human fibroblasts were cultured on 13 mm diameter (Thermanox polymer) cover slips retained in a two part support (Minucell Minusheets). Tissues present in the healing wound that must survive and proliferate were represented by the cells within the chamber. Nutrient medium (DMEM with 5% FCS with 1% Buffer All) to simulate an irrigant fluid/wound exudate mixture was pumped from a reservoir into the lower aspect of the chamber where it bathed the fibroblasts and was removed from the upper aspect of the chamber and returned to a second reservoir. The wound chamber was maintained at less than atmospheric pressure by means of a Vacuum pump in line with the circuit.

The pumps for the circuit were peristaltic pumps acting on silicone (or equivalent) elastic tubing. The circuit was exposed to a vacuum of no more than 10% atmospheric pressure (950 mbar and atmospheric pressure varied up to a maximum value. of 1044 mbar.) The internal diameter of the tubing was 1.0 mm. A total volume for the circuit including the chamber and the reservoir was between 50 and 220 ml. The flow rates used were at 0.2 ml$^{-1}$.

The circuit also comprised upstream of the wound chamber, a heat exchanger such that the temperature of the nutrient media bathing the cells reaches between 35° C. and 37° C.

Experiments were conducted that simulated conditions not uncommon for healing wounds whereby the chamber simulating the wound was subjected >to stimulation QY ultrasound waves representing the Exogen Ultrasound (Smith & Nephew) device signal for a period of time not greater than 20 min. These experiments were performed using both sequential (SEQ) and simultaneous (SIA) irrigation/aspiration.

Method in More Detail

Using simultaneous irrigate/aspirate (SIA) and sequential irrigate/aspirate (SEQ) systems the effect of ultrasound treatment on fibroblast proliferation was determined.

Cells

Human dermal fibroblasts (HS8/BS04) grown at 37° C./5% $CO_2$, in T175 flasks containing 35 ml DMEM/10% FCS media were washed in PBS and lifted using 1× trypsin/EDTA (37° C. for 5 min). Trypsin inhibition was achieved by adding 10 ml DMEM/10% FCS media and the cells pelleted by centrifugation (Hereus Megafuge 1.0R; 1000 rpm for 5 min). The media was discarded and cells re-suspended in 10 ml DMEM/10% FCS. Cells were counted using haemocytometer and diluted in DMEM/10% FCS to obtain 100,000 cells per ml.

Cells (100 µl of diluted stock) were transferred to 13 mm Thermanox tissue culture coated cover slips (cat. 174950, lot 591430) in a 24 well plate and incubated at 37° C. in 5% $CO^2$ to allow for cell adherence. After 1 h, 1 ml DMEM/10% FCS media was added per well and the cells incubated for approximately 5 hours in the above conditions. Cells were serum starved overnight by removing the DMEM/10% FCS and washing the coverslips with 2×1 ml PBS prior to the addition of 1 ml DMEM/O % FCS.

Following overnight incubation, cells were assessed visually for cell adherence under the microscope and those with good adherence were inserted into cover slip holders for assembly in the Minucell chamber. A number of coverslips (n=6) were removed to determine the baseline WST activity.

Media

Cells were grown in DMEM media (Sigma, no. 06429) supplemented with 5% foetal calf serum; 1-glutamine, non-essential amino acids and penicillin/streptomycin (various lot numbers). Media used in the experimental systems was buffered with Buffer-All media (Sigma, lot 51k2311) to ensure stable pH of the media.

Minucell Flow Systems

Media (50 ml) was transferred to each bottle prior to the autoclaved systems being assembled. The Minucell chambers were filled with 4 ml media prior to coverslips being inserted. The systems were set-up as shown in FIG. 1 (pump 1, asset 5715; pump 2, asset 4586 set to run at 0.2 ml/min; hot plates asset were set to 45° C.; Discofix 3-way valves (Arnolds lot 04A2092042 c/z); vacuum pump, llmvac VCZ 310 (set to 950 mbar).

SEQ Systems (i.e. Sequential Irrigation/Aspiration)

Media was pumped through the systems at 0.2 ml/min continuously when the chambers were full. The Minucell chambers were emptied by disconnecting the tubing from the pump and switching the 3-way valve to allow air through an attached 0.22 µm filter. When fully emptied, the 3-way valve was switched to close the system between the valve and the pump and so allowing the formation of a vacuum in the system. Elevation of the 66 3-way valve ensured media did not pass through the 0.22 µm filter by gravity flow. After 1 h, the 3-way valve was switched back to the starting position to allow the Minucell chamber to fill and the tube reconnected to the pump. The SEQ systems were treated as per Table 1.

TABLE 1

FILL/EMPTY REGIME FOR SEQ SYSTEM MINUCELL CHAMBERS

| | Time (h) | | | | | | | | | | | | |
|---|---|---|---|---|---|---|---|---|---|---|---|---|---|
| | 0 | 1 | 2 | 3 | 4 | 5 | 6 | 7 | 8 | 20 | 21 | 22 | 23 | 24 |
| Empty/fill | F | E | F | E | F | E | F | E | F | E | F | E | W | A |

F, full chamber, flowing;
E, empty chamber, under vacuum;
W, remove coverslips for WST assay;
A, read WST assay result.

SIA Systems (i.e. Simultaneous Irrigate/Aspirate)

Continuous irrigate aspirate systems were run for 24 h with media irrigating the cells and being aspirated under vacuum set to 950 mbar. The atmospheric pressure varied daily, up to a maximum value of 1048 mbar, therefore the difference in pressure between the systems and the atmosphere was always under 10%.

Ultrasound Treatment

Whilst media was circulating through the Minucell systems in the first hour, Minucell chambers were placed onto the ultrasound device using transducers. The Minucell chambers received 20 minutes ultrasound treatment and were then placed on the hot-plates. The optimal intensity and wavelength for delivery to each Minucell chamber was determined to be 1.5 MHz at a power (intensity) of 100 MW/$CM^2$. The ultrasound properties would generally have to be optimised for any particular application or wound dressing to take account of the properties of the wound and the dressing involved. The values used in the present invention were at a relatively high intensity to compensate for the relatively high attenuation in the experimental apparatus.

WST Assay

WST assay to measure the cells mitochondrial activity was performed on the coverslips. WST reagent (Roche, lot 11264000) was diluted to 10% v/v in DMEM/10% FCS/buffer all media. The coverslips (n=6) were removed from each Minucell chamber and washed in 1 ml PBS. PBS was removed and 200 µl WST/DMEM media added. The coverslips were then incubated at 37° C. for 45 min before transferring 150 µl to a 96 well plate. The absorbance at 450 nm with reference at 655 nm was determined using Ascent Multiskan Microtitre plate reader.

Results and Discussion

The mitochondrial activity of cells grown in SIA and SEQ systems, with or without ultrasound treatment was determined using the WST assay.

The WST activity of individual experiments is shown in Table 2. In both the SIA and SEQ systems, the 20 min of ultrasound treatment stimulated fibroblast proliferation, as determined by WST assay. Fibroblast proliferation was greater in the SIA system compared to SEQ system, which reflects data obtained previously. The summarized data in Table 2 shows the stimulatory effect of ultrasound treatment was observed a number of times i.e. in 3 repetitions.

TABLE 2

| Conditions | Mean of cell activity* after 25 hours. N = 3 |
| --- | --- |
| Continuous flow (SIA) flow | 0.19 |
| Continuous flow (SIA) plus) ultrasound | 0.23 |
| Fill empty 6 cycles | 0.05 |
| Fill empty 6 cycles plus ultrasound | 0.11 |

*Cell activity measured with a WST (Tetrazolium based mitochondrial dehdrogenase activity assay).

Treatment of fibroblasts with 20 min ultrasound signal increased rate of proliferation after 24 hours.

The effect was observed in both SIA and SEQ flow systems.

Fibroblast activity in ultrasound stimulated SEQ system was still less than fibroblast activity in the un-stimulated SIA system.

Although the ultrasound signal stimulated fibroblast proliferation in the SEQ system above that of the un-stimulated control system, the level of fibroblast activity was still lower than the fibroblast activity determined in the un-stimulated SIA.

This experiment demonstrates the beneficial effects of applying ultrasound to a wound bed as it encourages the activity and proliferation of cell, thus promoting healing.

What is claimed is:

1. A wound dressing comprising:
a backing layer configured to be positioned over a wound and form a closure over the wound;
a boss configured to reinforce the backing layer;
a first tube configured to pass through the backing layer and the boss, a first end of the first tube configured to be disposed outside a volume at least partially enclosed by the backing layer, and a second end of the first tube configured to be disposed in the volume at least partially enclosed by the backing layer; and
an ultrasonic transducer mounted on the boss by one or more struts positioned only at edges of the ultrasonic transducer, the ultrasonic transducer spaced apart from the boss by the one or more struts to form at least one fluid flow channel between the boss and the ultrasonic transducer, the at least one fluid flow channel configured to be in fluid communication with the second end of the first tube and further configured to complete a fluid flow path from the first end of the first tube to the wound.

2. The wound dressing of claim 1, wherein the ultrasonic transducer is mounted on a surface of the boss configured to face the wound.

3. The wound dressing of claim 1, wherein a portion of the boss is configured to extend through the backing layer.

4. The wound dressing of claim 1, further comprising a manifold comprising a plurality of apertures in fluid communication with the first tube.

5. The wound dressing of claim 4, wherein the manifold comprises a tree of tubules that fluidically connects the plurality of apertures to the first tube.

6. The wound dressing of claim 1, further comprising a wound filler configured to be disposed in the wound under backing layer.

7. The wound dressing of claim 6, further comprising a wound contact layer configured to be positioned below the wound filler in direct contact with the wound and further configured to conform to shape of the wound, the wound contact layer comprising a plurality of openings configured to allow fluid to pass through the wound contact layer.

8. The wound dressing of claim 1, further comprising a second tube configured to pass through the backing layer and the boss, a first end of the second tube configured to be disposed outside the volume at least partially enclosed by the backing layer, and a second end of the second tube configured to be disposed in the volume at least partially enclosed by the backing layer.

9. The wound dressing of claim 8, wherein the second tube is configured to be positioned adjacent the backing layer and extend radially in the volume at least partially enclosed by the backing layer.

10. A kit comprising the wound dressing of claim 8 and a negative pressure source configured to be in fluid communication with the first or second tube.

* * * * *